US008481486B2

(12) United States Patent
Saghatelyan et al.

(10) Patent No.: US 8,481,486 B2
(45) Date of Patent: Jul. 9, 2013

(54) METHODS OF TREATING NEUROLOGICAL DISEASES BY REGULATING MIGRATION OF NEUROBLASTS IN THE ADULT NERVOUS SYSTEM WITH TENASCIN-R

(75) Inventors: Armen Saghatelyan, Gif-sur-Yvette (FR); Antoine de Chevigny, Paris (FR); Pierre-Marie Lledo, Antony (FR)

(73) Assignee: Institut Pasteur, Paris (FR)

( * ) Notice: Subject to any disclaimer, the term of this patent is extended or adjusted under 35 U.S.C. 154(b) by 1062 days.

(21) Appl. No.: 12/232,307

(22) Filed: Sep. 15, 2008

(65) Prior Publication Data

US 2009/0136565 A1 May 28, 2009

Related U.S. Application Data

(62) Division of application No. 11/078,479, filed on Mar. 14, 2005, now Pat. No. 7,432,251.

(51) Int. Cl.
*A61K 38/18* (2006.01)
(52) U.S. Cl.
USPC .............................. 514/8.3; 514/7.6; 530/350
(58) Field of Classification Search
None
See application file for complete search history.

(56) References Cited

U.S. PATENT DOCUMENTS

| 2003/0165485 A1 | 9/2003 | Bertilsson et al. |
| 2006/0159652 A1* | 7/2006 | Gagnon et al. ............... 424/85.1 |

FOREIGN PATENT DOCUMENTS

| WO | WO 96/28550 | * 9/1996 |
| WO | WO 03/039575 | 5/2003 |

OTHER PUBLICATIONS

Pesheva et al., The Journal of Cell Biology, vol. 109, Oct. 1989 1765-1778.*
Ahlskog, J.E., "Cerebral Transplantation for Parkinson's Disease: Current Progress and Future Prospects," *Mayo Clin. Proc.* 68:578-91 (1993).
Eberhardt, O. et al., "Gene Therapy in Parkinson's Disease," *Cell Tissue Res.* 318:243-60 (2004).
Freed, W.J. et al., "Transplanted Adrenal Chromaffin Cells in Rat Brain Reduce Lesion-Induced Rotational Behavior," *Nature* 292:351-52 (1981).
Madrazo, I. et al., "Open Microsurgical Autograft of Adrenal Medulla to the Right Caudate Nucleus in Two Patients with Intractable Parkinson's Disease," *New Eng. J. Med.* 361:831-34 (1987).
Pasheva, P. et al., "The Yin and Yang of Tenascin-R in CNS Development and Pathology," *Progress in Neurobiology* 61:465-93 (2000).

* cited by examiner

*Primary Examiner* — Jim Ketter
(74) *Attorney, Agent, or Firm* — Finnegan, Henderson, Farabow, Garrett & Dunner, L.L.P.

(57) ABSTRACT

This invention provides a method for regulating migration of neuronal progenitor cells in the nervous system of a mammal. The method comprises providing a mammal with TNR, a biologically active fragment of TNR, or a TNR agonist in an amount sufficient to direct migration of the neuronal progenitor cells. The invention provides a method of treating neurological diseases by replenishing diseased, damaged, or destroyed neural cells in the central nervous system or in the peripheral nervous system.

16 Claims, 13 Drawing Sheets
(9 of 13 Drawing Sheet(s) Filed in Color)

ccttggtttc cgttgcagat tcccacaact ccatgctgtg tgctgcaggc
tggtcctgaa cccagatctc tggctgagag gatggggca gatgggaaa
cagtggttct gaagaacatg ctcattggcg tcaacctgat ccttctgggc
tccatgatca agccttcaga gtgtcagctg gaggtcacca cagaaagggt
ccagagacag tcagtggagg aggagggagg cattgccaac tacaacacgt
ccagcaaaga gcagcctgtg gtcttcaacc acgtgtacaa cattaacgtg
cccttggaca acctctgctc ctcagggcta gaggcctctg ctgagcagga
ggtgagtgca gaagacgaga ctctggcaga gtacatgggc cagacctcag
accacgagag ccaggtcacc tttacacaca ggatcaactt ccccaaaaag
gcctgtccat gtgccagttc agcccaggtg ctgcaggagc tgctgagccg
gatcgagatg ctggagaggg aggtgtcggt gctgcgagac cagtgcaacg
ccaactgctg ccaagaaagt gctgccacag gacaactgga ctatatccct
cactgcagtg gccacggcaa ctttagcttt gagtcctgtg gctgcatctg
caacgaaggc tggtttggca agaattgctc ggagccctac tgcccgctgg
gttgctccag ccgggggtg tgtgtggatg ccagtgcat ctgtgacagc
gaatacagcg gggatgactg ttccgaactc cggtgcccaa cagactgcag
ctcccggggg ctctgcgtgg acggggagtg tgtctgtgaa gagccctaca
ctggcgagga ctgcagggaa ctgaggtgcc ctggggactg ttcggggaag
gggagatgtg ccaacggtac ctgtttatgc gaggagggct acgttggtga
ggactgcggc cagcggcagt gtctgaatgc ctgcagtggg cgaggacaat
gtgaggaggg gctctgcgtc tgtgaagagg gctaccaggg ccctgactgc
tcagcagttg cccctccaga ggacttgcga gtggctggta tcagcgacag
gtccattgag ctggaatggg acgggccgat ggcagtgacg gaatatgtga
tctcttacca gccgacggcc ctgggggcc tccagctcca gcagcgggtg
cctggagatt ggagtggtgt caccatcacg gagctggagc caggtctcac
ctacaacatc agcgtctacg ctgtcattag caacatcctc agccttccca
tcactgccaa ggtggccacc catctctcca ctcctcaagg gctacaattt
aagacgatca cagagaccac cgtggaggtg cagtgggagc ccttctcatt
ttccttcgat gggtgggaaa tcagcttcat tccaaagaac aatgaagggg
gagtgattgc tcaggtcccc agcgatgtta cgtcctttaa ccagacagga
ctaaagcctg gggaggaata cattgtcaat gtggtggctc tgaaagaaca
ggcccgcagc ccccctacct cggccagcgt ctccacagtc attgacggcc
ccacgcagat cctggttcgc gatgtctcgg acaccgtggc ttttgtggag
tggattcccc ctcgagccaa agtcgatttc attctttga aatatggcct
ggtgggcggg gaaggtggga ggaccacctt ccggctgcag cctcccctga
gccaatactc agtgcaggcc ctgcggcctg ctcccgata cgaggtgtca
gtcagtgccg tccgagggac caacgagagc gattctgcca ccactcagtt
cacaacagag atcgatgccc ccaagaactt gcgagttggt tctcgcacag
caaccagcct tgacctcgag tgggataaca gtgaagccga agttcaggag
tacaaggttg tgtacagcac cctggcgggt gagcaatatc atgaggtact
ggtccccagg ggcattggtc caaccaccag ggccaccctg acagatctgg
tacctggcac tgagtatgga gttggaatat ctgccgtcat gaactcacag
caaagcgtgc cagccaccat gaatgccagg actgaacttg acagtcccg

```
agacctcatg gtgacagcct cctcggagac ctccatctcc ctcatctgga
ccaaggccag tggccccatt gaccactacc gaattacctt taccccatcc
tctgggattg cctcagaagt caccgtaccc aaggacagga cctcatacac
actaacagat ctagagcctg gggcagagta catcatttcc gtcactgctg
agaggggtcg gcagcagagc ttggagtcca ctgtggatgc tttcacaggc
ttccgtccca tctctcatct gcacttttct catgtgacct cctccagtgt
gaacatcact tggagtgatc catctcccc agcagacaga ctcattctta
actacagccc cagggatgag gaggaagaga tgatggaggt ctccctggat
gccaccaaga ggcatgctgt cctgatgggc ctgcaaccag ccacagagta
tattgtgaac cttgtggctg tccatggcac agtgacctct gagcccattg
tgggctccat caccacagga attgatcccc caaaagacat cacaattagc
aatgtgacca aggactcagt gatggtctcc tggagccctc ctgttgcatc
tttcgattac taccgagtat catatcgacc cacccaagtg ggacgactag
acagctcagt ggtgcccaac actgtgacag aattcaccat caccagactg
aacccagcta ccgaatacga aatcagcctc aacagcgtgc ggggcaggga
ggaaagcgag cgcatctgta ctcttgtgca cacagccatg acaaccctg
tggatctgat tgctaccaat atcactccaa cagaagccct gctgcagtgg
aaggcaccag tgggtgaggt ggagaactac gtcattgttc ttacacactt
tgcagtcgct ggagagacca tccttgttga cggagtcagt gaggaatttc
ggcttgttga cctgcttcct agcacccact atactgccac catgtatgcc
accaatggac ctctcaccag tggcaccatc agcaccaact tttctactct
cctggaccct ccggcaaacc tgacagccag tgaagtcacc agacaaagtg
ccctgatctc ctggcagcct cccagggcag agattgaaaa ttatgtcttg
acctacaaat ccaccgacgg aagccgcaag gagctgattg tggatgcaga
agacacctgg attcgactgg agggcctgtt ggagaacaca gactacacgg
tgctcctgca ggcagcacag gacaccacgt ggagcagcat cacctccacc
gctttcacca caggaggccg ggtgttccct catccccaag actgtgccca
gcatttgatg aatggagaca ctttgagtgg ggtttacccc atcttcctca
atggggagct gagccagaaa ttacaagtgt actgtgatat gaccaccgac
gggggcggct ggattgtatt ccagaggcgg cagaatggcc aaactgattt
tttccggaaa tgggctgatt accgtgttgg cttcgggaac gtggaggatg
agttctggct ggggctggac aatatacaca ggatcacatc ccagggccgc
tatgagctgc gcgtggacat gcgggatggc caggaggccg ccttcgcctc
ctacgacagg ttctctgtcg aggacagcag aaacctgtac aaactccgca
taggaagcta caacggcact gcgggggact ccctcagcta tcatcaagga
cgccctttct ccacagagga tagagacaat gatgttgcag tgactaactg
tgccatgtcg tacaagggag catggtggta taagaactgc accggacca
acctcaatgg gaagtacggg gagtccaggc acagtcaggg catcaactgg
taccattgga aaggccatga gttctccatc ccctttgtgg aaatgaagat
gcgcccctac aaccaccgtc tcatggcagg gagaaaacgg cagtccttac
agttctgagc agtgggcggc tgcaagccaa ccaatatttt ctgtcatttg
tttgtatttt ataatatgaa acaagggggg agggtaatag caatgtgttt
tgcaacatat taagagtatg tgaaggaagc agggatgtcg caggaatccg
ctggctaaca tctgctcttg gtttctgctg ccctggagcc tgaccctcag
```

FIGURE 1B

```
tctccattct ccctcctacc caggcctcct caaccttcac ctcctttccc
accaaggagg agaagtagga agttttctta aagggccaat tcaaagccaa
gtcgtggggt gcagattgtt atggtgacag gcacacacat ttttctaccc
ttcttctgag atgtcctctg ccttccaggt atttgtgatt ttgtcacagc
ctgacatggc caggttctca cactggccca gagaaaagag cctcagcaag
agagttttgc caacaattcc ccttaaaagg aaacagatca actacaccgc
atcccaacaa cccaggttct tttccttcct tccttccttc ctcccttcct
tctttcctgc cttccc
```

FIGURE 1C

```
MGADGETVVLKNMLIGVNLILLGSMIKPSECQLEVTTERVQRQSVEEEGG
IANYNTSSKEQPVVFNHVYNINVPLDNLCSSGLEASAEQEVSAEDETLAE
YMGQTSDHESQVTFTHRINFPKKACPCASSAQVLQELLSRIEMLEREVSV
LRDQCNANCCQESAATGQLDYIPHCSGHGNFSFESCGCICNEGWFGKNCS
EPYCPLGCSSRGVCVDGQCICDSEYSGDDCSELRCPTDCSSRGLCVDGEC
VCEEPYTGEDCRELRCPGDCSGKGRCANGTCLCEEGYVGEDCGQRQCLNA
CSGRGQCEEGLCVCEEGYQGPDCSAVAPPEDLRVAGISDRSIELEWDGPM
AVTEYVISYQPTALGGLQLQQRVPGDWSGVTITELEPGLTYNISVYAVIS
NILSLPITAKVATHLSTPQGLQFKTITETTVEVQWEPFSFSFDGWEISFI
PKNNEGGVIAQVPSDVTSFNQTGLKPGEEYIVNVVALKEQARSPPTSASV
STVIDGPTQILVRDVSDTVAFVEWIPPRAKVDFILLKYGLVGGEGGRTTF
RLQPPLSQYSVQALRPGSRYEVSVSAVRGTNESDSATTQFTTEIDAPKNL
RVGSRTATSLDLEWDNSEAEVQEYKVVYSTLAGEQYHEVLVPRGIGPTTR
ATLTDLVPGTEYGVGISAVMNSQQSVPATMNARTELDSPRDLMVTASSET
SISLIWTKASGPIDHYRITFTPSSGIASEVTVPKDRTSYTLTDLEPGAEY
IISVTAERGRQQSLESTVDAFTGFRPISHLHFSHVTSSSVNITWSDPSPP
ADRLILNYSPRDEEEEMMEVSLDATKRHAVLMGLQPATEYIVNLVAVHGT
VTSEPIVGSITTGIDPPKDITISNVTKDSVMVSWSPPVASFDYYRVSYRP
TQVGRLDSSVVPNTVTEFTITRLNPATEYEISLNSVRGREESERICTLVH
TAMDNPVDLIATNITPTEALLQWKAPVGEVENYVIVLTHFAVAGETILVD
GVSEEFRLVDLLPSTHYTATMYATNGPLTSGTISTNFSTLLDPPANLTAS
EVTRQSALISWQPPRAEIENYVLTYKSTDGSRKELIVDAEDTWIRLEGLL
ENTDYTVLLQAAQDTTWSSITSTAFTTGGRVFPHPQDCAQHLMNGDTLSG
VYPIFLNGELSQKLQVYCDMTTDGGGWIVFQRRQNGQTDFFRKWADYRVG
FGNVEDEFWLGLDNIHRITSQGRYELRVDMRDGQEAAFASYDRFSVEDSR
NLYKLRIGSYNGTAGDSLSYHQGRPFSTEDRDNDVAVTNCAMSYKGAWWY
KNCHRTNLNGKYGESRHSQGINWYHWKGHEFSIPFVEMKMRPYNHRLMAG
RKRQSLQF
```

FIGURE 2

METHODS OF TREATING NEUROLOGICAL DISEASES BY REGULATING MIGRATION OF NEUROBLASTS IN THE ADULT NERVOUS SYSTEM WITH TENASCIN-R

This is a division of application Ser. No. 11/078,479, filed Mar. 14, 2005, now U.S. Pat. No. 7,432,251, which is incorporated herein by reference.

FIELD OF THE INVENTION

This invention relates to the use of tenascin-R (TNR) to modulate migration of neural cells in the central nervous system (CNS) or peripheral nervous system (PNS). More particularly, this invention relates to methods of exposing a patient suffering from a disorder of the nervous system to TNR and achieving regulation of neuronal precursor migration in the patient's CNS or PNS to reduce at least one symptom of the disorder.

BACKGROUND OF THE INVENTION

The olfactory bulb (OB) is one of the few structures in the adult forebrain in which there is a continuous supply of newborn neurons (Luskin, 1993; Alvarez-Buylla, et al., 2002). The neural progenitors, which originate from stem cells located in the subventricular zone (SVZ) of the lateral ventricles, follow an intricate path of migration before reaching their final position in the OB. First, they migrate tangentially, in chains, along the entire extent of the rostral migratory stream (RMS), and once in the bulb, turn to migrate radially out of the RMS into the outer layers, where they differentiate into inhibitory interneurons (Luskin, 1993; Alvarez-Buylla, et al., 2002).

Despite increasing knowledge on the origin, proliferation, and tangential migration of neuroblasts, the way by which they achieve their radial migration to functionally integrate into the bulbar circuitry remains elusive. Interestingly, radial glia, which are central for axonal guidance and radial migration during development, are no more present in the adult OB (Alvarez-Buylla, et al., 2002). This implies that neuroblasts arriving in the rostral extension of the RMS of adult forebrain follow unique migratory pathways, quite distinct from those observed at perinatal stages. Although a recent report has provided evidence that the OB-derived extracellular matrix (ECM) molecule reelin affects detachment of neuroblasts from chains, once they have reached the OB (Hack, et al., 2002), the identity of the cues halting tangential migration, initiating detachment of neuroblasts from the RMS and facilitating their radial migration have yet to be characterized. Furthermore, the impact of sensory experience in these processes needs to be examined.

The ability to generate neurons in the adult brain is relevant to the development of therapeutic strategies aimed at directing the migration and individualization of endogenous and/or grafted progenitor cells. Recently, it has been demonstrated that endogenous adult stem cells have the ability to regenerate functional neurons in non-neurogenic diseased areas (Magavi et al., 2000; Arvidsson, et al., 2002; Nakatomi, et al., 2002). Neuronal progenitors migrate to the damaged areas from the neurogenic source localized in the SVZ suggesting that not only increased proliferative activity following brain damage (Arvidsson, et al., 2002; Nakatomi, et al., 2002), but also changes either in the migratory capabilities of neuroblasts and/or in the microenvironment of the target tissues may help to recruit the newly generated neurons for repair. According to this invention, recruitment of neuronal progenitors in diseased areas of the nervous system can be considerably enhanced by application of TNR.

A better understanding of neural migration provides the basis for new treatments for neurological disease and damage, which are needed in the art. This invention aids in fulfilling this need.

SUMMARY OF THE INVENTION

This invention resulted from an investigation of the possibility that reoriented migration of neuroblasts in the core of the OB is orchestrated by a gradient of extracellular cues surrounding the RMS within the OB. It was discovered that the expression pattern of the ECM molecule tenascin-R (TNR) would be compatible with such a functional role: mice lacking a functional TNR gene demonstrate an accumulation of neuroblasts in the $RMS_{OB}$, indicating a defect of radial migration in the OB. Furthermore, in vivo and in vitro, neuroblasts migrate towards cells that have been engineered to express TNR. Thus, this invention relies on the ability of TNR to modulate the migration of neuroblasts.

More particularly, this invention provides a method for regulating migration of endogenous or exogenous newborn neuronal cells in the central nervous system or peripheral nervous system of a mammal suffering from a disease or damage to alleviate a symptom or symptoms of the disease or damage by administering TNR to the mammal. Administration of TNR in the extracellular space of a damaged or diseased central nervous system or peripheral nervous system tissue can induce endogenous or grafted neural progenitor cells to migrate towards this site for tissue repair by cell replacement or by creating a better microenvironment for already existing cells.

The invention also provides for a method of treating a neurological disease by regulating migration of neural cells in the central or peripheral nervous system by administering a composition comprising TNR, or a fragment, derivative, or analog of TNR, and inducing the neuronal cells to migrate to the region of disease or damage.

Furthermore, the invention provides a pharmaceutical composition for treating neurological disease, which comprises TNR, a fragment, derivative, or analog of TNR, and a pharmaceutically acceptable carrier. In aspects of the invention, this pharmaceutical composition enhances the permeability of the ventricle wall.

In another aspect, the invention provides a screening test for a molecule that regulates neuronal cell migration by administering a candidate molecule to a TNR-deficient mouse, observing neuronal cell migration, and comparing neuronal cell migration to migration in a non-treated TNR-deficient mouse. A difference in the neuronal cell migration between the treated and non-treated mice indicates that the molecule regulates neuronal cell migration.

BRIEF DESCRIPTION OF THE DRAWINGS

The patent or application file contains at least one drawing executed in color. Copies of this patent or patent application publication with color drawings will be provided by the Office upon request and payment of the necessary fee.

This invention will be described in detail with reference to the drawings in which:

FIGS. 1A-C: cDNA sequence of human TNR (SEQ ID NO: 1).

FIG. 2: Amino acid sequence of human TNR (SEQ ID NO: 2).

(e, g) Quantification of the number of neuroblasts de-routed from the SVZ (e) and RMS (g) by non-transfected (Ctrl) and TNR-transfected BHK cells (TNR). **, P<0.001. Scale bars: b and c, 200 and 50 µm for left and right panels, respectively; d and f, 20 µm.

Figure 10:
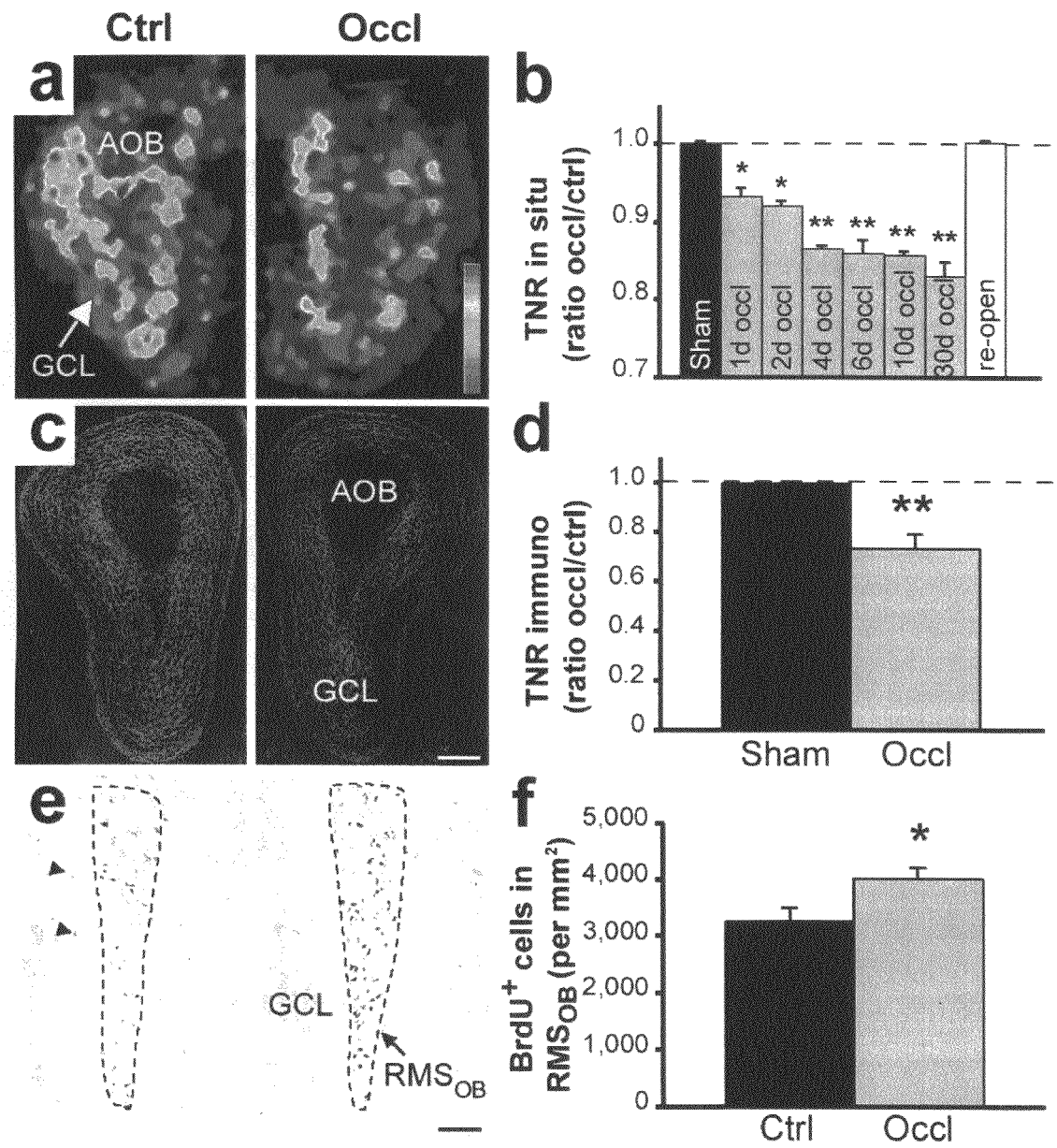

FIG. 10: Activity-dependent expression of TNR in the OB. (a) Pseudocolor images showing expression of TNR mRNA in a coronal section through the OB receiving inputs from nostrils that had been open (Ctrl) or closed (Occl) for 10 days. The images were obtained by β-imager with the exposure time of 20 hours. Note the decreased expression of TNR mRNA in the odor-deprived OB. (b) The effect of sensory deprivation on TNR mRNA expression was calculated by relating the mean radioactivity (in cpm/mm$^2$) of occluded bulb to that of control one. The measurements were performed at least from 20-30 coronal sections per animals and they were two to three animals per group. (c) TNR immunostaining of a coronal section through the OB receiving inputs from open (Ctrl) and closed (Occl) nostrils, 20 days following unilateral odor deprivation. Note decreased immunostaining for TNR in the GCL of the odor-deprived bulb. (d) The ratio of mean fluorescent intensity (per mm$^2$) in the GCL of occluded bulb to that of control bulb in TNR immunostained sections (n=6 animals). (e) BrdU+ cells in the RMS$_{OB}$ of control and occluded bulbs two days following BrdU injection. Unilateral sensory deprivation was performed 30 days before BrdU injection. The sections were counterstained with methyl green and arrowheads indicate BrdU+ cells in the GCL. (f) Quantification of BrdU+ nuclei in the RMS$_{OB}$ of control (Ctrl) and occluded (Occl) bulbs indicates a significant increase in the density of newborn cells following sensory deprivation. * and ** indicate significant differences of P<0.05 and P<0.01, respectively. Scale bars: c, 200 µm and e, 50 µm.

Figure 11:
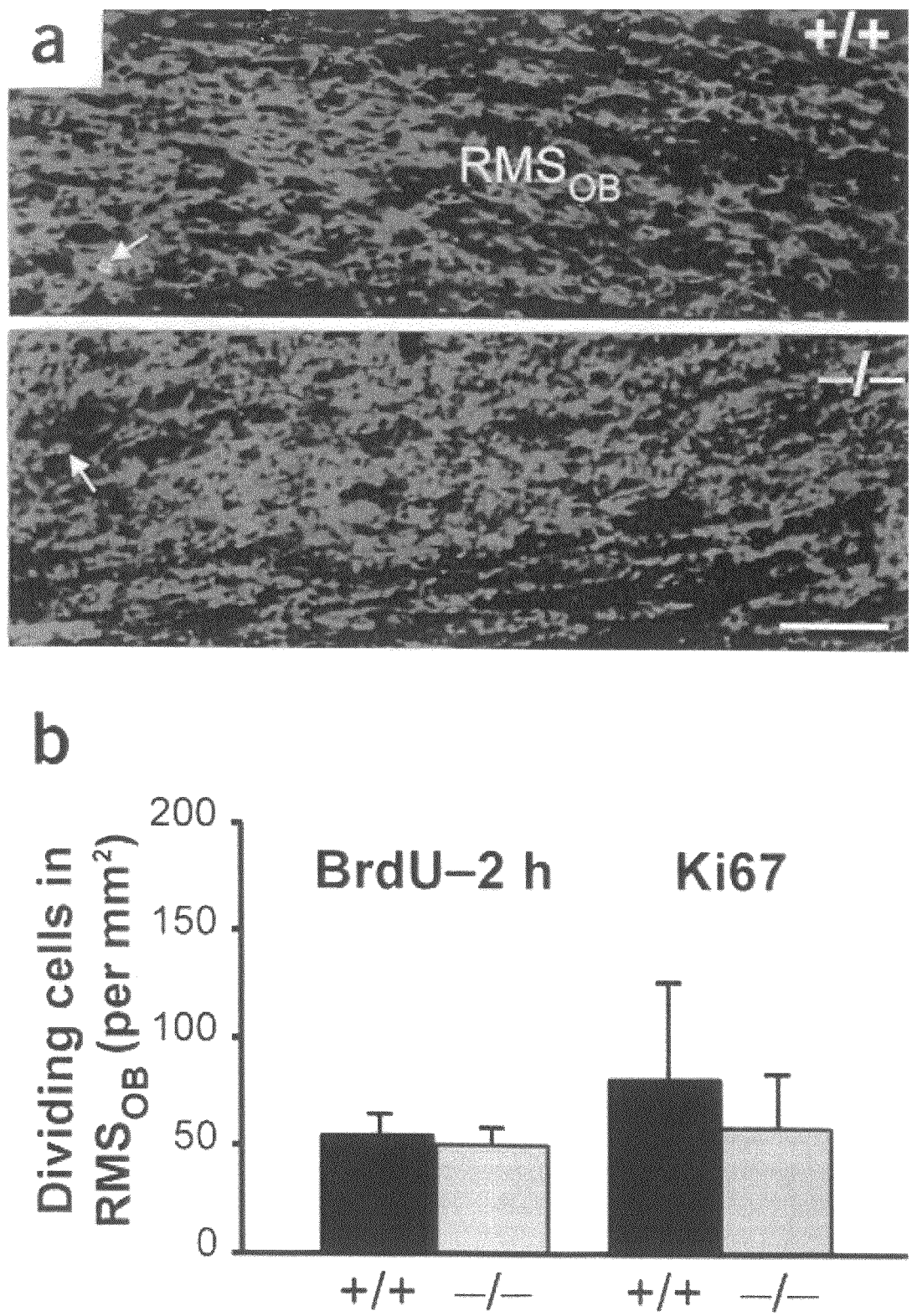

FIG. 11: Normal proliferation in the RMS$_{OB}$ of TNR-deficient mice. (a) PSA-NCAM (green) and BrdU (red) immunostaining in the RMS$_{OB}$ of control and TNR-deficient mice two hours following BrdU injection. Note the very low numbers of BrdU+ cells (arrows) in the two groups. (b) Quantification of BrdU+ cells two hours following BrdU injection and the proliferative marker Ki67+ cells in the RMS$_{OB}$ of control and TNR-deficient mice reveal no difference in the proliferation rates between the two genotypes. Data are presented as means±SEM. Scale bars: a, 50 µm.

DETAILED DESCRIPTION OF THE INVENTION

Neuroblasts born in the adult forebrain that travel to the olfactory bulb (OB) use two modes of migration: tangentially, along the rostral migratory stream, and radially, in the core of the OB where they start to ascend to the outer layers. While the mechanisms of tangential migration have been extensively studied, the factors controlling radial migration remain unexplored.

TNR is a member of the tenascin gene family and is composed of cysteine-rich amino terminal region, epidermal growth factor-like domains, fibronectin-type III homologous repeats, and a domain homologous to fibrinogen (Jones and Jones, 2000). TNR appears to be restricted to the CNS and is expressed by differentiating oligodendrocytes and some inhibitory interneurons at late embryonic stages (Jones and Jones, 2000; Fuss, et al., 1993). The functions of TNR are manifold: TNR binds to voltage-dependent Na$^+$-channels (Srinivasan, et al., 1998; Xiao et al., 1999) and conductance velocity of action potential is reduced in TNR-deficient mice (Weber, et al., 1999). Also, TNR is an important constituent of perineuronal nets surrounding many, but not all, inhibitory interneurons (Bruckner, et al., 2000) and organization of perineuronal nets is perturbed in TNR-deficient mice. Additionally, it has been shown that TNR-deficient mice display alterations in the organization of symmetric, presumably inhibitory, perisomatic synapses (Nikonenko, et al., 2003) as well as synaptic transmission and plasticity in the CA1 region of hippocampus (Saghatelyan, et al., 2001).

It has now been discovered that TNR, expressed in the adult mouse OB, initiates both the detachment of neuroblasts from chains and their radial migration. Expression of TNR is neuronal activity-dependent, since it is drastically reduced by odor deprivation. Furthermore, grafting of TNR-transfected cells into non-neurogenic regions de-routes migrating neuroblasts toward these regions. The identification of an extracellular microenvironment capable of directing migrating neuroblasts provides insights into the mechanisms regulating radial migration away from the RMS into the outer layer of the adult OB, thus offering a promising tool for cell replacement therapies.

It has been shown that TNR can enhance or decrease neurite outgrowth and neuronal adhesion depending on the cell type and association of TNR with other ECM molecules (Pesheva and Probstmeier, 2000). Furthermore, TNR has been found to defasciculate axons of cerebellar granule cells in vitro, thus possibly allowing inhibitory interneurons to invade the tightly fasciculating bundles of axonal processes (Xiao et al., 1998). These observations are pertinent in view of the fact that TNR induces detachment of neuroblasts from chains in the core of OB and initiates their radial migration into the outer layers. Similarly, reelin has been reported to influence this process in the adult OB (Hack et al., 2002). TNR and reelin could share the same signaling pathway to induce detachment of neuroblasts from chains. Therefore, the effect on SVZ explants of transfected cells expressing TNR may be comparable with that obtained in presence of transfected cells expressing TNR and reelin. Nevertheless, while reelin affects only detachment of neuroblasts (Hack, et al., 2002), TNR also acts as a directional cue that de-routes neuronal progenitors from their tangential migratory pathway. These results indicate that either TNR activates two independent pathways used separately for neuroblasts detachment and their radial reorientation (the former might be also used by reelin), or it acts via a unique pathway that is different from that used by reelin.

TNR can act directly by interacting with particular cellular receptors present on migrating neuroblasts, or indirectly, together with other ECM associated molecules, by capturing and presenting some growth factors (Boudreau and Bissell, 1998) necessary for radial migration. Among cell surface receptors for TNR are contactin/F3 (Pesheva et al., 1993), acetylated gangliosides that influence phosphorylation of focal adhesion kinases and affect integrin function (Probstmeier, et al., 1999) and receptor protein-tyrosine phosphatases belonging to the family of chondroitin sulfate proteoglycans (CSPGs) (Xiao, et al., 1997; Milev, et al., 1998). While the involvements of contactin/F3 and CSPGs, the latter being highly expressed in the adult RMS (Thomas, et al., 1996), remain to be explored in adult neurogenesis, it has been recently shown that integrins are not involved in the radial migration of neuroblasts to the OB (Murase, et al., 2002). Interestingly, initiation of radial migration in the adult OB correlates with the appearance of NMDA receptor (NMDAR)-mediated currents (Carleton, et al., 2003). These receptors are involved in neuronal migration during early developmental stages (Komuro and Rakic, 1993). Thus, TNR, via its cell surface receptor(s), can trigger the expression of functional NMDARs and, as a consequence, radial migration. Alternatively, TNR can also directly interact with NMDARs through a mechanism similar to that described for $GABA_BRs$ (Saghatelyan, et al., 2003), and thus control radial migration more directly. Regardless of the mechanism, TNR plays a specific and important role in the initiation of radial migration of newborn neurons in the adult forebrain.

It is believed that target structures provide attractive and/or survival factors for developing neuronal networks (Kennedy and Tessier-Lavigne, 1995; Svendsen and Sofroniew, 1996) and that these factors can be regulated in an activity-dependent manner. For instance, in the olfactory system, modulation of odor information flow has been reported to affect the survival of newborn neurons: sensory deprivation by nostril occlusion reduces granule cell number in the developing (Frazier and Brunjes, 1998; Brunjes, 1994; Cummings and Brunjes, 1997) and adult OB (Henegar and Maruniak, 1991), whereas re-opening the nostril following early occlusion (Cummings and Brunjes, 1997), as well as olfactory enrichment in adults (Rochefort et al., 2002) increases the number of newly formed bulbar interneurons. Thus, in addition to the reduced survival of newborn neurons following nostril occlusion, odor deprivation also impairs radial migration of neuroblasts from the RMS to the OB, via downregulation of TNR expression, further demonstrating that TNR is an important mediator relaying network activity to the recruitment of newborn neurons into the OB.

As indicated above, the present invention relates to the administration of TNR to modulate the migration of neural cells as a therapy for central nervous system or peripheral nervous system disease, disorder, or damage.

As used herein, the term "modulate" or the term "regulate" refers to having an effect in such a way as to alter the migration of a neural cell, such as, but not limited to a neural stem cell (NSC) or neural progenitor cell, also called neural precursor cells (NPC). As used herein, the term "migrate" refers to movement of a neural cell from one region of the central or peripheral nervous system to another.

NSCs can be identified by their ability to undergo continuous cellular proliferation, to regenerate exact copies of themselves (self-renew), to generate a large number of regional cellular progeny, and to elaborate new cells in response to injury or disease. NPCs mean cells that can generate progeny that are either neuronal cells (such as neuronal precursors or mature neurons) or glial cells (such as glial precursors, mature astrocytes, or mature oligodendrocytes). Typically, the cells express some of the phenotypic markers that are characteristic of the neural lineage. They also do not usually produce progeny of other embryonic germ layers when cultured by themselves in vitro unless dedifferentiated or reprogrammed in some fashion. As used herein, the term "neurosphere" refers to the ball of cells consisting of NSCs and NPCs.

The tenascins are a family of large extracellular matrix glycoproteins that comprise five known members (tenascin-C, tenascin-R (TNR), tenascin-X, tenascin-Y, and tenascin-W). All members of this family, except TN-W, have been shown to occur in multiple isoforms due to alternative splicing. TNR appears in many molecular forms with the predominant ones displaying apparent molecular masses of 220, 200, 180, and 160 kD (Kruse et al., Nature, 316:146-48, 1985).

The human TNR cDNA sequence is provided in FIG. 1. The human TNR amino acid sequence is provided in FIG. 2.

As used herein, the term "administering" refers to any action that results in the presence of TNR in an area where its action on neuronal cell migration is expected. "Administration" can include, but is not limited to, methods of infusion, methods of expressing TNR in cells, for example by gene therapy, or other methods of providing TNR to a region.

In embodiments of the invention, the TNR administered to a patient can be any of the molecular forms of TNR in which TNR naturally occurs or as biologically active fragments of these molecular forms. In a preferred embodiment TNR is 220, 200, 280, or 160 kD. In a more preferred embodiment, the 180 kD TNR is administered.

The invention also pertains to variants of TNR that function as agonists (mimetics). Variants of TNR can be generated by mutagenesis, e.g., discrete point mutations. In contrast, an agonist can retain substantially the same, or a subset of, the biological activities of the naturally occurring protein. An antagonist can inhibit one or more of the activities of naturally occurring protein by, for example, competitively binding to the receptor. Thus, specific biological effects can be elicited by treatment with a variant having a limited function. In one embodiment, treatment of a subject with a variant having a subset of the biological activities of the naturally occurring form of TNR has fewer side effects in a subject relative to treatment with the naturally occurring form of the TNR.

Preferably, the analog, variant, or derivative TNR is functionally active. As utilized herein, the term "functionally active" refers to species displaying one or more known functional attributes of a full-length TNR. A "variant" refers to protein or peptide that differs from naturally occurring TNR, but that retains essential properties thereof.

In one embodiment of the invention, TNR is administered as an isolated, purified protein. This protein can be recombinantly produced, purified, and formulated according to well known methods or it can be chemically synthesized.

In one embodiment, TNR proteins or biologically active peptides of TNR may be synthesized for administration to a patient. A variety of protein synthesis methods are common in the art, including synthesis using a peptide synthesizer. See, e.g., Bodansky, ed., 1988; Merrifield, 1986; Barany, et al., 1987; Kent, 1988; Daiser, et al., 1989.

Chemical synthesis of peptides facilitates the incorporation of modified or unnatural amino acids, including D-amino acids and other small organic molecules. Replacement of one or more L-amino acids in a peptide with the corresponding D-amino acid isoforms can be used to increase the resistance of peptides to enzymatic hydrolysis, and to enhance one or more properties of biologically active peptides, e.g., receptor binding, functional potency or duration of action. In addition, the introduction of covalent cross-links into a peptide sequence can conformationally and topographically constrain the peptide backbone. This strategy can be used to develop peptide analogs of TNR, or fragments, derivatives, or analogs thereof, with increased potency, selectivity, and stability.

In an alternative embodiment, TNR or a biologically active fragment of TNR may be obtained by methods well-known in the art for recombinant peptide expression and purification using the known sequence of the TNR cDNA. Optionally, the nucleic acid molecule reciting this sequence or a fragment of it can include additional sequences, for example, but not limited to restriction enzyme recognition sites that facilitate cloning into a suitable cloning vector, such as a plasmid. The nucleic acid may be DNA, RNA, or a combination thereof. Nucleic acids encoding the TNR, or fragments, derivatives, or analogs thereof, may be obtained by any method known within the art (e.g., by PCR amplification using synthetic primers hybridizable to the 3'- and 5'-termini of the sequence and/or by cloning from a cDNA or genomic library using an oligonucleotide sequence specific for the given gene sequence, or the like). Alternatively, nucleic acids can also be generated by chemical synthesis.

In another embodiment of the invention, any of the methodologies known for the insertion of nucleic acid fragments into a vector may be used to construct expression vectors that contain a chimeric gene comprised of the appropriate transcriptional/translational control signals and TNR-coding sequences. Promoter/enhancer sequences within expression vectors may use regulatory sequences from organisms such as, but not limited to, plants, animals, insects, or fungi.

A host cell for the expression of TNR or biologically active fragments of TNR can be any prokaryotic or eukaryotic cell. For example, the protein or peptide can be expressed in bacterial cells, including, but not limited to, E. coli, insect cells, fungi or mammalian cells (such as Chinese hamster ovary cells (CHO), baby hamster kidney cells (BHK cells), or COS cells). Other suitable host cells are known to those skilled in the art. In one embodiment, a nucleic acid encoding a TNR, or a fragment, derivative, or analog thereof, is expressed in mammalian cells using a mammalian expression vector. Examples of mammalian expression vectors include pCDM8 (Seed, 1987) and pMT2PC (Kaufman et al., 1987).

The host cells can be used to produce (e.g., overexpress) peptide in culture. Accordingly, the invention further provides methods for producing the TNR protein or biologically active fragments of TNR using the host cells of the invention. In one embodiment, the method comprises culturing the host cell of invention (into which a recombinant expression vector encoding the peptide has been introduced) in a suitable medium such that protein or peptide is produced. The method further involves isolating peptide from the medium or the host cell. (Ausubel et al., 1998)

An "isolated" or "purified" recombinant peptide or biologically active portion thereof is substantially free of cellular material or other contaminating proteins from the cell or tissue source from which the peptide of interest is derived. The language "substantially free of cellular material" includes preparations in which the peptide is separated from cellular components of the cells from which it is isolated or recombinantly produced. In one embodiment, the language "substantially free of cellular material" includes preparations of peptide having less than about 30% (by dry weight) of peptide (also referred to herein as a "contaminating protein") other than the desired peptide, more preferably less than about 20% of contaminating protein, still more preferably less than about 10% of contaminating protein, and most preferably less than about 5% contaminating protein. When the peptide or biologically active portion thereof is recombinantly produced, it is also preferably substantially free of culture medium, e.g., culture medium represents less than about 20%, more preferably less than about 10%, and most preferably less than about 5% of the volume of the peptide preparation.

Variants of TNR that function as either agonists (mimetics) or as antagonists can be identified by screening libraries of mutants of TNR for agonist or antagonist activity. In one embodiment, a variegated library of variants is generated by combinatorial mutagenesis at the nucleic acid level and is encoded by a variegated gene library. A variegated library of variants can be produced by, for example, enzymatically ligating a mixture of synthetic oligonucleotides into gene sequences such that a degenerate set of potential sequences is expressible as individual peptides, or alternatively, as a set of larger fusion proteins (e.g., for phage display) containing the set of sequences therein. There are a variety of methods that can be used to produce libraries of potential variants from a degenerate oligonucleotide sequence. Chemical synthesis of a degenerate gene sequence can be performed in an automatic DNA synthesizer and the synthetic gene then ligated into an appropriate expression vector. Use of a degenerate set of genes allows for the provision, in one mixture, of all of the sequences encoding the desired set of potential sequences. Methods for synthesizing degenerate oligonucleotides are known in the art. See, e.g., Narang, 1983; Itakura et al., 1984a; Itakura et al., 1984b; Ike et al., 1983.

Derivatives and analogs of TNR or individual moieties can be produced by various methods known within the art. For example, the polypeptide sequences may be modified by any number of methods known within the art. See e.g., Sambrook, et al., 1990. Modifications include: glycosylation, acetylation, phosphorylation, amidation, derivatization by known protecting/blocking groups, linkage to an antibody molecule or other cellular reagent, and the like. Any of the numerous chemical modification methodologies known within the art may be utilized including, but not limited to, specific chemical cleavage by cyanogen bromide, trypsin, chymotrypsin, papain, V8 protease, $NaBH_4$, acetylation, formylation, oxidation, reduction, metabolic synthesis in the presence of tunicamycin, etc.

Derivatives and analogs may be full length or other than full length, if said derivative or analog contains a modified nucleic acid or amino acid, as described infra. Derivatives or analogs of the TNR include, but are not limited to, molecules comprising regions that are substantially homologous in various embodiments, of at least 30%, 40%, 50%, 60%, 70%, 80%, 90% or preferably 95% amino acid identity when: (i) compared to an amino acid sequence of identical size; (ii) compared to an aligned sequence in that the alignment is done by a computer homology program known within the art (e.g., Wisconsin GCG software) or (iii) the encoding nucleic acid is capable of hybridizing to a sequence encoding the aforementioned peptides under stringent (preferred), moderately stringent, or non-stringent conditions. See, e.g., Ausubel, et al., 1993.

Derivatives of TNR may be produced by alteration of its sequence by substitutions, additions, or deletions that result in functionally-equivalent molecules. One or more amino acid residues within TNR may be substituted by another amino acid of a similar polarity and net charge, thus resulting in a silent alteration. Conservative substitutes for an amino acid within the sequence may be selected from other members of the class to which the amino acid belongs. For example, nonpolar (hydrophobic) amino acids include alanine, leucine, isoleucine, valine, proline, phenylalanine, tryptophan and methionine. Polar neutral amino acids include glycine, serine, threonine, cysteine, tyrosine, asparagine, and glutamine. Positively charged (basic) amino acids include arginine, lysine and histidine. Negatively charged (acidic) amino acids include aspartic acid and glutamic acid.

As an alternative to administering TNR as a purified, isolated protein or peptide, the invention provides for the administration of TNR, a functionally active fragment of TNR, a derivative of TNR, or an analog of TNR as a protein or peptide expressed from a recombinant cell introduced into the patient's central or peripheral nervous system. In this embodiment, the nucleotides encoding TNR, or a fragment, derivative, or analog of TNR, can be inserted into the mammalian cells using any in vitro nucleotide transfer procedure.

The invention encompasses using several different cell types to express TNR, a fragment of TNR, a derivative of TNR, or an analog of TNR. These include, but are not limited to, all glial cell types, neuronal embryo cells, and neuronal stem cells. Preferably, these cells expressing TNR, or a fragment, derivative or analog thereof, are derived from the same patient into whom the cells are to be administered.

In vitro gene transfer can be carrier out by, for example, but not limited to, chemical methods, such as calcium phosphate mediated transfection; physical methods, such as electroporation, microinjection, and particle bombardment; fusion methods, such as by the use of liposomes; receptor-mediated endocytosis; and recombinant viruses, such as adenovirus, adeno-associated virus (AAV), herpes simplex virus, human immunodeficiency virus, maloney murine leukemia virus, and vaccinia virus.

It will be understood that replication defective viruses can be used as gene transfer vectors. Defective replication means that such viruses are not infectious in the absence of a helper virus that can supply missing viral genes to complete the viral life cycle. A helper cell line that contains integrated provirus sequences that supply viral structural proteins can be employed for this purpose.

When a retroviral vector is employed for gene transfer, the retroviral vector can be constructed by discarding the protein coding sequences of the retroviral genome (gag, pot, and env), and replacing by heterologous coding sequences, while retaining essential cis-acting elements. These essential elements include a packaging signal sequence that ensures the encapsidation of the vector RNA into virions (Psi in murine vectors or E in avian systems); elements that are necessary to direct the process of reverse transcription, such as the primer binding site (PBS), which binds the tRNA primer of reverse transcription, terminal repeat (R) sequences that guide the reverse transcriptase between RNA strands during DNA synthesis; a purine-rich sequence 5' of the 3' LTR that serves as the priming site for synthesis of the second (plus) DNA strand; and specific sequences near the ends of the LTRs that are necessary for integration of the vector DNA into the host cell chromosome in the ordered and reproducible manner characteristic of retroviruses.

A retroviral packaging cell line can be employed to provide the viral helper functions, which have been deleted from the vector genome, namely the gag, pol, and env proteins. These helper functions should be stably expressed in the packaging cells from one or more helper plasmids whose RNA transcripts are not efficiently packaged into viral particles because they lack the packaging signal sequence. When a vector genome is transfected into such packaging cells, the viral gag proteins recognize and package the vector RNA genome into viral particles, which are released into the culture supernatant. Viral particles can be collected from the supernatants.

Other vectors can be used besides retroviral vectors, including those derived from DNA viruses, such as simian virus (SV40), bovine papilloma viruses, and also polyoma and herpes viruses. The cells can be expanded in number before or after insertion of the nucleotides encoding TNR, or a fragment, a derivative, or an analog thereof, independent of the method employed to transfer the nucleotides to the mammalian somatic cell.

The marker nucleotides can be any nucleotides encoding TNR or other marker nucleotides. Examples of such marker nucleotides include neoR, multi-drug resistant nucleotides, thymidine kinase nucleotides, beta-galactosidase, dihydrofolate reductase (DHFR), and chloroamphenicol acetyl transferase. The marker nucleotides can be inserted into a mammalian cell together with nucleotides encoding TNR, or a fragment, derivative, or analog thereof, or separately. The marker nucleotides and the therapeutic nucleotides can also be one and the same, namely, nucleotides encoding TNR, or a fragment, derivative, or analog thereof. Dual gene constructs in which one of the genes encodes an antibiotic resistance marker offer the advantage that the TNR-transduced target cells in a culture can be selected from a background of non-transduced cells.

Gene therapy vectors can be delivered to a subject by, for example, intravenous injection, local administration (see U.S. Pat. No. 5,328,470) or by stereotactic injection (see e.g., Chen et al., 1994). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system.

The procedure is performed in such a manner that upon transfer into the host, the cells will produce the TNR, or a fragment, derivative, or analog thereof, in the host, preferably at the site of administration or proximate thereto. The TNR, or a fragment, derivative, or analog thereof, should be produced in an amount sufficient and under conditions that modulate a biological function in the recipient. Thus, for example, in the case of a neurological disorder, the cells containing nucleotides encoding the TNR, TNR fragment, TNR derivative, or TNR analog, should be transplanted into a neurological site, such as the brain, and expressed TNR should be secreted from the cells into extracellular medium in sufficient amounts to affect neurological function. Short-term expression of TNR at basal levels in the recipient is generally adequate.

In embodiments of the invention, TNR, a biologically active fragment of TNR, a derivative of TNR, or an analog of TNR can be administered locally to any loci implicated in the CNS disorder pathology, e.g. any loci where (or close to the place where) neural cells are suffering. Attracted newborn cells can repair the damaged tissue or alternatively can produce survival factors that will reduce neuronal cell death. For example, TNR, a biologically active fragment of TNR, or an agonist of TNR can be administered locally to the sites including, but not limited to, the volume adjacent to the lateral wall, the hippocampus, alveus, ventricle of the brain, substantia nigra, striatum, locus ceruleous, nucleus basalis of Meynert, pedunculopontine nucleus, cerebral cortex, spinal cord and retina, or any region of tissue that is impaired by stroke injury, ischemic injury, or injury due to any disease.

In embodiments of the invention, TNR, a biologically active form of TNR, or a TNR agonist is administered in an amount of 0.001 ng/kg/day to 10 mg/kg/day, preferably in an amount of 0.01 ng/kg/day to 5 mg/kg/day, more preferably in an amount of 0.1 ng/kg/day to 1 mg/kg/day and most preferably in an amount of 0.1 ng/kg/day to 1 µg/kg/day, in a volume of 0.0001 to 10 ml. The administration can be local or systemic and can optionally be in a combination with a ventricle wall permeability increasing factor, or in combination with a locally or systemically co-administered agent.

In embodiments of the invention, TNR, a biologically active form of TNR, or an agonist of TNR, or a host cell expressing any of these, is administered by intraventricularly, intravenously, intraarterially, intracerebroventricularly, intraparenchymally, intrathecally, or intracranially.

Neural stem cells and their progeny can be induced to migrate in vivo by administering TNR, a biologically active fragment of TNR, or a TNR agonist to the host, alone or in combination with other agents in a pharmaceutical composition that will induce proliferation, differentiation, and survival of the cells. Pharmaceutical compositions include any substance that blocks the inhibitory influence and/or stimulates neural stem cells and stem cell progeny to migrate and/or survive. Such in vivo manipulation allows new cells to (i) endogenously or exogenously replace those lost due to injury or disease, thus obviating the need for transplanting foreign cells into a patient, or (ii) create a molecular microenvironment that rescues any damaged or injured tissue.

In embodiments of the invention, the neural stem cell or neural progenitor cell is derived from fetal brain, adult brain, neural cell culture, a neurosphere, tissue enclosed by dura mater, peripheral nerves, ganglia, pancreas, skin, muscle, adult bone marrow, umbilical cord tissue and umbilical cord blood.

The invention relates to the treatment of a "neurological disease, disorder, or damage," which is a disease, damage, or disorder that results in the disturbance in the structure or function of the central pr peripheral nervous system resulting from developmental abnormality, disease, injury or toxin. Examples of neurological diseases or disorders include, but are not limited to, neurodegenerative disorders (e.g. associated with Parkinson's disease or Parkinsonian disorders, Alzheimer's disease, Huntington's disease, Shy-Drager Syndrome, Progressive Supranuclear Palsy, Lewy Body Disease or Amyotrophic Lateral Sclerosis); ischemic disorders (e.g. cerebral or spinal cord infarction and ischemia, stroke); traumas (e.g. caused by physical injury or surgery, and compression injuries; affective disorders (e.g. stress, depression and post-traumatic depression); neuropsychiatric disorders (e.g. schizophrenia or other psychoses, multiple sclerosis or epilepsy); and learning and memory disorders.

In other embodiments of the invention, the disease or disorder of the nervous system is selected from the group consisting of cancer-related brain/spinal cord injury or diseases or disorders of the nervous system, including, but not limited to, lissencephaly syndrome, depression, bipolar depression/disorder, anxiety syndromes/disorders, phobias, stress and related syndromes, cognitive function disorders, aggression, drug and alcohol abuse, obsessive compulsive behavior syndromes, seasonal mood disorder, borderline personality disorder, cerebral palsy, drug addictions, multi-infarct dementia, Lewy body dementia, age related/geriatric dementia, epilepsy and injury related to epilepsy, temporal lobe epilepsy, brain injury, trauma related brain/spinal cord injury, anticancer treatment related brain/spinal cord tissue injury, infection and inflammation related brain/spinal cord injury, environmental toxin related brain/spinal cord injury, autism, attention deficit disorders, narcolepsy, and sleep disorders.

In embodiments of the invention, the reference to disease, damage, or disorder of the nervous system is selected from the group consisting of neurodegenerative disorders, neural stem cell disorders, neural progenitor disorders, ischemic disorders, neurological traumas, affective disorders, neuropsychiatric disorders, degenerative diseases of the retina, retinal injury/trauma and learning and memory disorders.

This invention provides a method of treating a neurological disease, damage, or disorder comprising administering TNR, a biologically active form of TNR, or an agonist or antagonist of TNR that modulates neural stem cell or neural progenitor cell migration in vivo to a mammal. The term "mammal" refers to any animal classified as a mammal, including humans, cows, horses, dogs, sheep and cats. In a preferred embodiment, the mammal is a human.

The treatments encompassed by the invention may be administered in a therapeutic or prophylactic manner. Therapeutics that may be utilized include, but are not limited to: (i) an aforementioned protein or peptide, analog, derivative, fragment, or homolog thereof; (ii) antibodies to an aforementioned protein or peptide; (iii) nucleic acids encoding an aforementioned protein or peptide; (iv) administration of antisense nucleic acid and nucleic acids that are "dysfunctional" (e.g., due to a heterologous insertion within the coding sequences of coding sequences to an aforementioned peptide) that are utilized to "knockout" endogenous function of an aforementioned protein or peptide by homologous recombination; or (v) modulators (e.g., inhibitors, agonists and antagonists, including additional peptide mimetic of the invention or antibodies specific to a protein or peptide of the invention) that alter the interaction between an aforementioned protein or peptide and its binding partner.

In various embodiments of the invention, suitable in vitro or in vivo assays are performed to determine the effect of a specific therapeutic and whether its administration is indicated for treatment of the affected tissue. In various specific embodiments, in vitro assays may be performed with representative stem cells or newly differentiated cells involved in the patient's disorder, to determine if a given therapeutic exerts the desired effect upon the cell type(s). Compounds for use in therapy may be tested in suitable animal model systems including, but not limited to rats, mice, chicken, cows, monkeys, rabbits, and the like, prior to testing in the mammalian subject of the treatment. Similarly, for in vivo testing, any of the animal model system known in the art may be used prior to administration to human subjects.

A pharmaceutical composition useful as a therapeutic agent for the treatment of central or peripheral nervous system disorders is provided. For example, the composition includes TNR, a biologically active fragment of TNR, or an agonist of TNR, which can be administered alone or in combination with the systemic or local co-administration of one or more additional agents. Such agents include preservatives, ventricle wall permeability increasing factors, stem cell mitogens, survival factors, glial lineage preventing agents, anti-apoptotic agents, anti-stress medications, neuroprotectants, and anti-pyrogenics. The pharmaceutical composition preferentially treats CNS diseases by stimulating cells (e.g., ependymal cells and subventricular zone cells) to migrate, targeting loci where cells are damaged or missing.

A pharmaceutical composition of the invention is formulated to be compatible with its intended route of administration. Solutions or suspensions used for administration can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™. (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., chimeric peptide) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

In one embodiment, the active TNR-related compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active TNR-related compound calculated to produce the desired therapeutic effect in association with the required pharmaceutical carrier. The specification for the dosage unit form of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

Preferably the TNR, or fragment, derivative, or analog thereof, is formulated in a medium providing maximum stability and the least formulation-related side-effects. In addition to TNR, or fragment, derivative, or analog thereof, the composition of the invention will typically include one or more protein carrier, buffer, isotonic salt, and stabilizer.

In some instances, the TNR, a biologically active fragment of TNR, or an agonist of TNR can be administered by a surgical procedure implanting a catheter coupled to a pump device. The pump device can also be implanted or be extracorporally positioned. Administration of TNR, or a fragment, derivative, or analog thereof, can be in intermittent pulses or as a continuous infusion. Devices for injection to discrete areas of the brain are known in the art (see, e.g., U.S. Pat. Nos. 6,042,579; 5,832,932; and 4,692,147).

Compositions can be administered in any conventional form for administration of a protein. A composition can be administered in any manner known in the art in which it may either pass through or by-pass the blood-brain barrier. Methods for allowing factors to pass through the blood-brain barrier include minimizing the size of the factor, providing hydrophobic factors that may pass through more easily, conjugating the protein or other molecule to a carrier molecule that has a substantial permeability coefficient across the blood brain barrier (see, e.g., U.S. Pat. No. 5,670,477).

TNR, biologically active fragments of TNR, or TNR agonists, derivatives, and co-administered agents can be incorporated into pharmaceutical compositions suitable for administration. Such compositions typically comprise the agent and a pharmaceutically acceptable carrier. As used herein, "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the TNR-related active compound, use thereof in the compositions is contemplated. Supplementary active compounds can also be incorporated into the compositions. Modifications can be made to the agents to affect solubility or clearance of the peptide. Peptidic molecules may also be synthesized with D-amino acids to increase resistance to enzymatic degradation. In some cases, the composition can be co-administered with one or more solubilizing agents, preservatives, and permeation enhancing agents.

For example, the composition can include a preservative or a carrier such as proteins, carbohydrates, and compounds to increase the density of the pharmaceutical composition. The composition can also include isotonic salts and redox-control agents.

In some embodiments, the composition administered includes TNR, or a fragment, derivative, or analog thereof, and one or more agents that increase the permeability of the ventricle wall, e.g. "ventricle wall permeability enhancers." Such a composition can help an injected composition penetrate deeper than the ventricle wall. Examples of suitable ventricle wall permeability enhancers include, for example, liposomes, VEGF (vascular endothelial growth factor), IL-s, TNFα, polyoxyethylene, polyoxyethylene ethers of fatty acids, sorbitan monooleate, sorbitan monolaurate, polyoxyethylene monolaurate, polyoxyethylene sorbitan monolaurate, fusidic acid and derivatives thereof, EDTA, disodium EDTA, cholic acid and derivatives, deoxycholic acid, glycocholic acid, glycodeoxycholic acid, taurocholic acid, taurodeoxycholic acid, sodium cholate, sodium glycocholate, glycocholate, sodium deoxycholate, sodium taurocholate, sodium glycodeoxycholate, sodium taurodeoxycholate, chenodeoxycholic acid, urosdeoxycholic acid, saponins, glycyrrhizic acid, ammonium glycyrrhizide, decamethonium, decamethonium bromide, dodecyltrimethylammonium bromide, and dimethyl-β-cyclodextrin or other cyclodextrins.

The fact that neural stem cells are located in the tissues lining ventricles of mature brains offers several advantages for the modification and manipulation of these cells in vivo and the ultimate treatment of various neurological diseases, disorders, and injury that affect different regions of the CNS. Therapy for these diseases can be tailored accordingly so that stem cells surrounding ventricles near the affected region would be induced to migrate using the methods described herein.

The ventricular system is found in nearly all brain regions and thus allows easier access to the affected areas. In order to induce the stem cells to migrate in vivo by exposing them to a composition comprising TNR, a biologically active fragment of TNR, or an agonist of TNR, it is relatively easy to implant a device that administers the composition to the ventricle and, thus, to the neural stem cells. For example, a cannula attached to an osmotic pump may be used to deliver the composition. TNR should be delivered close to the ventricular system or alternatively between the ventricular system and the damaged tissue. Alternatively, the composition may be injected directly into the ventricles. The neural stem cell progeny can migrate into regions that have been damaged as a result of injury or disease. Furthermore, the close proximity of the ventricles to many brain regions would allow for the diffusion of a secreted neurological agent by the stem cells or their progeny.

In an additional embodiment, TNR, a biologically active fragment of TNR, or a TNR agonist is administered locally, as described above, in combination with an agent administered locally or systemically. Such agents include, for example, one or more stem cell mitogens, survival factors, differentiation factors, glial-lineage preventing agents, anti-apoptotic agents, anti-stress medications, neuroprotectants, and anti-pyrogenics, or any combination thereof.

The agent is administered systemically before, during, or after administration of the TNR, or fragment, derivative, or analog thereof. The locally administered agent can be administered before, during, or after TNR, or a fragment, derivative, or analog thereof, is administered.

For treatment of Huntington's Disease, Alzheimer's Disease, Parkinson's Disease, and other neurological disorders affecting primarily the forebrain, TNR, or a fragment, derivative, or analog thereof, alone or with an additional agent or agents can be delivered between the damaged or diseased area and the zone where neuroblasts are produced. For example, Parkinson's Disease is the result of low levels of dopamine in the brain, particularly the striatum. It is therefore advantageous to induce dopamine producing cells from either the patient's own cells or transplanted cells to migrate to the striatum, thus locally raising the levels of dopamine.

Normally the cell bodies of dopaminergic neurons are located in the substantia nigra and adjacent regions of the mesencephalon, with the axons projecting to the striatum. The methods and compositions of the invention provide an alternative to the use of drugs and the controversial use of large quantities of embryonic tissue for treatment of Parkinson's disease. Dopaminergic cells can be generated in the striatum by the administration of a composition comprising TNR, a biologically active fragment of TNR, or a TNR agonist.

For the treatment of MS and other demyelinating or hypomyelinating disorders, and for the treatment of Amyotrophic Lateral Sclerosis or other motor neuron diseases, TNR, a biologically active fragment of TNR, or a TNR agonist can be delivered either alone or with an additional agent or agents to the central canal.

In addition to treating CNS tissue immediately surrounding a ventricle, TNR, a biologically active fragment of TNR, or a TNR agonist, alone or with an additional agent or agents, can be administered to the lumbar cistern for circulation throughout the CNS.

In other aspects, neuroprotectants can also be co-administered systemically or locally before, during and/or after infusion of TNR, or a fragment, derivative, or analog thereof. Neuroprotectants include antioxidants (agents with reducing activity, e.g., selenium, vitamin E, vitamin C, glutathione, cysteine, flavinoids, quinolines, enzymes with reducing activity, etc), Ca-channel modulators, Na-channel modulators, glutamate receptor modulators, serotonin receptor agonists, phospholipids, unsaturated- and polyunsaturated fatty acids, estrogens and selective estrogen receptor modulators (SERMS), progestins, thyroid hormone and thyroid hormone-mimicking compounds, cyclosporin A and derivatives, thalidomide and derivatives, methylxanthines, MAO inhibitors; serotonin-, noradrenaline and dopamine uptake blockers; dopamine agonists, L-DOPA, nicotine and derivatives, and NO synthase modulators.

Certain components of the compositions of the invention may be pyrogenic following intravenous injection. Thus, in some aspects of the invention, antipyrogenic agents like cox2 inhibitors, indomethacin, salisylic acid derivatives and other general anti-inflammatory/anti-pyrogenic compounds can be systemically or locally administered before, during and/or after administration of a composition comprising TNR, a biologically active fragment of TNR, or a TNR agonist.

In another aspect of the invention, anti-apoptotic agents including caspase inhibitors and agents useful for antisense-modulation of apoptotic enzymes and factors can be administered before, during, or after administration of TNR, a biologically active fragment of TNR, or a TNR agonist.

Stress syndromes lower neurogenesis, therefore, in some aspects, it may be desirable to treat a subject with anti-stress medications such as, e.g., anti-glucocorticoids (e.g., RU486) and beta-blockers, administered systemically or locally before, during and/or after infusion of TNR, a biologically active fragment of TNR, or a TNR agonist.

Methods for preparing dosage forms are known, or will be apparent, to those skilled in this art.

The duration of treatment and time period of administration of TNR, or a fragment, derivative, or analog thereof, will also vary according to the size and condition of the patient, the severity of the illness and the specific composition and method being used.

The effectiveness of each of the foregoing methods for treating a patient with a CNS disease or disorder is assessed by any known standardized test for evaluating the disease.

In summary, it has now been demonstrated that (i) TNR is a key player in directing neuroblasts into their prospective target area, (ii) the level of TNR expression correlates strongly with olfactory sensory activity, and that (iii) grafting TNR-secreting cells into regions that do not receive progenitor neurons de-routes migrating neuroblasts to these areas. Thus, the activity-dependent recruitment of neuroblasts by TNR represents a fundamental mechanism through which neurogenesis in the adult OB is regulated and adapted to the level of sensory input. The TNR signaling pathway provides a novel approach for cell replacement therapies based on de-routing migrating cells.

Throughout this application, various publications are referenced in parentheses by author and year. Full citations for these references may be found at the end of the specification immediately preceding the sequence listing and the claims. The disclosure of these publications in their entireties are hereby incorporated by reference into this application to describe more fully the art to which this invention pertains.

The following examples are presented to demonstrate the methods of the present invention and to assist one of ordinary skill in using the same. The examples are not intended in any way to otherwise limit the scope of the disclosure.

Example 1

Animals

Two- to four-month-old TNR-deficient mice (Weber et al., 1999) and age-matched wild-type littermates were derived from heterozygous parents with a mixed C57BL/6J×129Ola background. Animals were kept on a 12 hour light-dark cycle at constant temperature (22° C.) with food and water ad libitum. Unilateral olfactory deprivation was performed on three- to four-month-old C57BL/6J mice by cauterizing one nostril (Meisami, 1976). All experimental procedures were in accordance with the Society for Neuroscience and European Union guidelines, and were approved by our institutional animal care and utilization committees.

BrdU Injections.

The DNA synthesis marker 5-bromo-2'-deoxyuridine (BrdU; Sigma) was dissolved in a sterile solution of 0.9% NaCl and 1.75% NaOH (0.4 N). This solution was injected intraperitoneally at a concentration of 50 mg/kg of body weight. BrdU containing cells were detected by immunohistochemistry after different survival times: A single dose of BrdU was given two hours prior to killing the animal to assess proliferation, or four hours to assess both proliferation and initial stages of migration. Two injections of BrdU spaced by four hours were done two days before sacrificing the animals to evaluate proliferation and migration of neuroblasts. Finally, four injections repeated every two hours were administrated to animals 21 days before sacrifice to evaluate proliferation, migration and survival of newborn cells.

Immunohistochemistry.

For all histological analyses requiring tissue fixation by perfusion, mice were deeply anesthetized with an overdose of sodium pentobarbital (100 mg/kg; Sanofi, Gentilly, France), and perfused intracardiacally with saline solution (0.9% NaCl) containing heparin ($5 \times 10^3$ units/ml) at 37° C., followed by 4% paraformaldehyde in 0.1 M phosphate buffer (pH 7.3). The brains were dissected out and immersed overnight in the same fixative at 4° C. Immunohistochemistry was performed on 40 μm-thick free-floating coronal or sagittal sections cut with a vibrating microtome (VT1000S, Leica, Rueil-Malmaison, France) and collected in PBS. Sections were first incubated overnight at 4° C. with the following monoclonal antibodies: mouse anti-TNR (clone 619; ref. 40), mouse anti-PSA and mouse anti-NeuN (Chemicon, Temecula, Calif.), mouse anti-Ki67 (Novocastra, Newcastle, England), rabbit anti-GFAP (Dako, Trappes, France) and rat anti-BrdU (Accurate Scientific, Harlan Sera-Lab, Loughborough, England).

To obtain BrdU immunostaining, the sections were pre-treated with 0.2% Triton X-100 for two hours, and the DNA was denaturated with 2N HCl for 30 min at 37° C. An overnight incubation with the anti-BrdU antibody at 4° C. was followed by a three-hour incubation at room temperature with biotinylated donkey anti-rat IgG antibodies, one hour in the avidin-biotin complex (ABC Kit, Vectastain Elite, Vector Laboratories, Burlingame, Calif.), and development with diaminobenzidine (DAB, 0.05%), to which 0.005% $H_2O_2$ was added. Double- and triple-labeling immunofluorescence was performed with the following fluorescent secondary antibodies: Alexa 568-labeled goat anti-rat IgG, Alexa 488-labeled goat anti-mouse IgG or IgM, and Cy5 anti-mouse IgG (Molecular Probes, Poortgebouw, Netherlands). Sections were analyzed using either a standard microscope (BX51; Olympus, Hamburg, Germany) for peroxidase staining or a Zeiss confocal microscope (Carl Zeiss S. A. S., Le Pecq, France) equipped with lasers Ar 488, HeNe1 543 and HeNe2 633, with LSM-510 software package for image acquisition and data analysis.

Terminal deoxynucleotidyl transferase-mediated biotinylated UTP nick end labeling (TUNEL) staining was performed in 8 μm thick coronal sections of the OB to detect DNA fragmentation in situ. After deparaffinization and rehydration, the tissue was treated with 0.5% Triton X-100 for 10 min, followed by incubation in equilibrium buffer (Serological Corporation, Norcross, Calif.). Sections were then incubated for 1 hour in a humidified chamber at 37° C., with a solution containing terminal deoxynucleotidyl transferase and digoxigenin nucleotides (Serological Corporation). After vigorous washing, a peroxidase labeled anti-digoxigenin antibody (Serological Corporation) was added for 30 min at room temperature, and staining was revealed by DAB.

The forebrains of unilaterally occluded mice were embedded in gelatin and cut in 40 μm thick coronal sections. Sections containing both bulbs, thus ipsi- and contralateral to the occluded nostril, were immunostained for TNR and TNR immunoreactivity was quantified by laser confocal microscopy using identical acquisition parameters for both bulbs.

In Situ Hybridization.

The fresh-frozen brains of sham and unilaterally odor-deprived mice were cut in 20 μm thick coronal slices. The sections containing control and occluded bulbs were thawed onto Superfrost Plus slides and stored at −80° C. until used. Hybridization was performed with the synthetic oligonucleotides (Eurogentec, Seraing, Belgium) 5' AAG CCC CTC CTT CCT CCT CCA CAG TTT GTC TCT GAG CCC TTT CTG 3' (SEQ ID NO: 3) complementary to nucleotides 720-764 of the mRNA encoding Mus musculus TNR (GenBank Accession No. NM-022312). The sequence of the probe was checked in a GenBank database search to exclude significant homology with other genes. The probe was labeled with [$^{33}$P]dATP (PerkinElmer, Mechelen, Germany) by using terminal deoxynucleotidyl transferase (Roche, Mannheim, Germany) reaction following the manufacturer's instructions. The sections were hybridized overnight at 42° C. in the hybridization mixture containing 50% formamide, 10% dextran sulfate, 4×SSC (1×SSC is 0.15M NaCl, 0.015M Na-citrate). Following hybridization, the sections were washed for 30 min in 1×SSC pre-warmed to 60° C., rinsed in 0.1×SSC and dehydrated in ascending concentration of ethanol. The digitalized autoradiograms were obtained by exposing sections in a β-imager (Biospace, Paris, France). This real-time imager provides rapid cartography of [$^{33}$P] labeling (in cpm/$mm^2$) in tissue sections.

TNR-Secreting Cells.

A 6.2 kb cDNA fragment containing nucleotides 1 to 4070 of the coding sequence of the 180 kD rat TNR protein was cloned into the XhoI site of the pcDNA3 vector (Invitrogen) for TNR expression under the control of the CMV promoter. For expression of the protein, the BHK cell line was transfected with 2 μg plasmid pcDNA3-TNR per well in a 6-well plate using the Lipofectamine kit (Invitrogen), following the manufacturer's instructions. Twenty four hours post-transfection TNR was detected by immunocytochemistry at the cell surface of the transfected cells, but not of the untransfected cells. Furthermore, culture supernatants were collected and analyzed for secretion of TNR by Western blotting. A specific immunoreactive band was seen at 180 kD in the supernatants of transfected, but not of non-transfected BHK cells.

SVZ Explant Cultures.

Cultures of SVZ explants were prepared as previously described (Fuss et al., 1993). Briefly, brains from P7 mice were dissected out and immersed in ice-cold HBSS medium (Gibco, Cergy Pontoise, France). The brains were cut in 200 μm thick sections, and those containing SVZ were selected for further manipulations. Under a surgical microscope, the SVZ was dissected along the lateral wall of lateral ventricles and then cut into small pieces (100-200 μm in diameter) that were transferred to 70% Matrigel (BD Bioscience, Le Pont de Claix, France). After polymerization of Matrigel at 37° C. for 10 min, neurobasal medium containing B27 supplement, L-glutamine (0.5 mM) and penicillin/streptomycin (1:1000) (all from Gibco) was added. Cultures were maintained in a humidified, 5% $CO_2$, 37° C. incubator. In some experiments, SVZ explants were co-cultured with aggregates of control or TNR-transfected BHK cells. Aggregates of BHK cells were prepared under low serum conditions using a hanging-drop method (Fan and Tessier-Lavigne, 1994).

Grafting Experiments.

Control and TNR-expressing BHK cells were labeled with the PKH26 red fluorescent cell linker kit (Sigma) following the manufacturer's instructions resulting in the staining of about 90% of all cells. Cells were grafted to the part of the striatum neighboring the SVZ (from bregma: anterio-posterior=1.5; medio-lateral=1.0; dorso-ventral=2.6) and just above the horizontal limb of RMS (anterio-posterior=3.35; medio-lateral=0.82; and dorso-ventral=3.0) using a Kopf stereotaxic apparatus (Harvard Apparatus, Les Ulis, France). On the day of transplantation, BHK cells were resuspended by trypsinization and collected after centrifugation (10 min, 475 g). For transplantation, animals were anesthetized with a ketamine/xylazine mixture (Sigma) and approximately $2 \times 10^5$ BHK cells in 0.3 μl of solution were injected over a time period of three minutes using a very thin glass electrode. The electrode was then left in place for an additional three minutes before being slowly withdrawn. Animals were killed four days later and the number of PSA-NCAM+ cells exiting the SVZ or RMS was counted in sagittal sections containing the grafts. The same sections were also processed for TNR immunolabeling.

Quantification and Statistical Analyses.

All quantifications were performed blind to the experimental conditions. For analysis of cell migration distance in vitro, explants were examined using phase-contrast microscopy after 20 hours in culture. Migration distance was quantified by measuring the maximum distance that cells had moved away from the perimeter of each explant.

BrdU immunostained nuclei were quantified in every third 40 μm section along the entire SVZ-OB pathway. To assess the number of newborn neurons in the OB, BrdU+ nuclei, observed with 20× and 40× objectives, were numbered for the entire granule cell and glomerular layers. The numbers of BrdU+ profiles were then related to the surface of granule cell (including mitral cell and internal plexiform layers) and glomerular layers. For RMS and SVZ, the density of BrdU+ cells was evaluated by relating the number of BrdU+ cells to the surfaces occupied by these cells. To count the number of TUNEL+ cells in the granule cell layer and $RMS_{OB}$, these areas were delineated manually on Methyl Green (Vector Laboratories, Burlingame, Calif.) counterstained sections. The percentage of BrdU/NeuN and BrdU/GFAP double immunostained cells were obtained by analyzing 3D reconstructed BrdU+ nuclei in the x-z and y-z orthogonal projections for the presence or absence of NeuN or GFAP.

The number of neuroblasts migrating towards the grafted BHK cells was quantified by counting the number of PSA-NCAM+ cells that had detached from the SVZ or RMS. In animals grafted with BHK cells secreting TNR, TNR-immunoreactive areas were as large as 100-400 μm in diameter. To assess the number of de-routed neuroblasts in BHK-injected mice, PSA-NCAM+ cells outside of their normal migratory pathway were counted in the 400 μm diameter area, calculated from the perimeter of the graft. Counting was done along the entire z axis, and data are presented as the total number of PSA-NCAM+ cells de-routed from the SVZ or the RMS.

To quantify the impact of sensory deprivation on TNR mRNA expression, the [$^{33}$P] activity (in $cpm/mm^2$) of occluded bulb was related to that of control bulb of the same section. To assess downregulation of TNR at protein level, the mean fluorescent intensity (per $mm^2$) of occluded bulb was related to that of control bulb of TNR immunostained sections.

All statistical comparisons between groups were made by using Student's t test.

Example 2

Expression of TNR in the Adult OB

Figure 3:
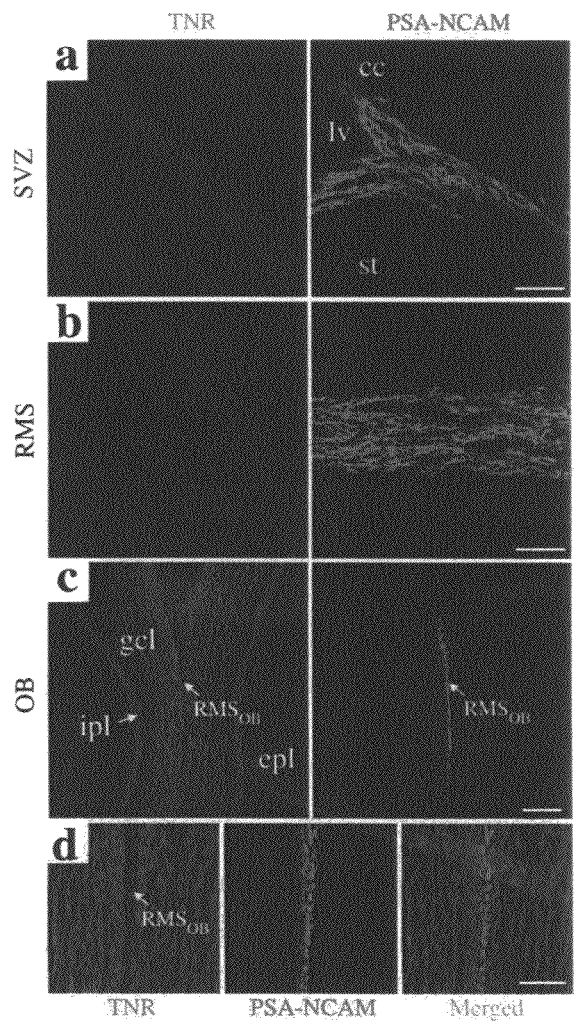
FIG. 3: Immunohistological detection of TNR in the SVZ-OB pathway of adult mice. Sagittal sections of (a) SVZ and (b) RMS immunostained for TNR (red) and PSA-NCAM (green). (c) Coronal section of OB stained for TNR (left panels) and PSA-NCAM (right panels). Note the absence of staining for TNR in the SVZ, RMS and $RMS_{OB}$, but presence in the GCL and IPL. (d) High magnification images of TNR and PSA-NCAM staining in the OB. Scale bars: a and b, 50 µm; c, 200 µm; d, 100 µm. CC, corpus callosum; EPL, external plexiform layer; IPL, internal plexiform layer; LV, lateral ventricle; $RMS_{OB}$, rostral migratory stream of the olfactory bulb; ST, striatum; SVZ, subventricular zone.

To examine the expression pattern of TNR in the adult mouse SVZ-OB system, immunofluorescence labeling was combined with confocal microscopy. At various magnifications, scanning through the successive sections from the SVZ to the OB (FIG. 3a-c) revealed strong TNR-positive (TNR+) staining, which was restricted to the granule cell and internal plexiform layers of the OB (FIGS. 3c and 3d). The SVZ and RMS, identified using antibodies against the polysialylated form of the neural cell adhesion molecule (PSA-NCAM), a marker for immature neurons (FIGS. 3a and 3b), were always devoid of TNR labeling. No staining for TNR was observed in the OB of TNR-deficient mice. The TNR immunostaining pattern is consistent with previous in situ hybridization data showing that granule cells are the major source of TNR synthesis in the adult OB (Fuss, et al., 1993). The exclusive pattern of TNR expression in the deep layers of the OB surrounding the RMS, and not within it, suggests a potential role of TNR in recruiting newborn neurons to the adult OB.

Example 3

Reduced Number of Newborn Cells in the OB of TNR-Deficient Mice

Figure 4:
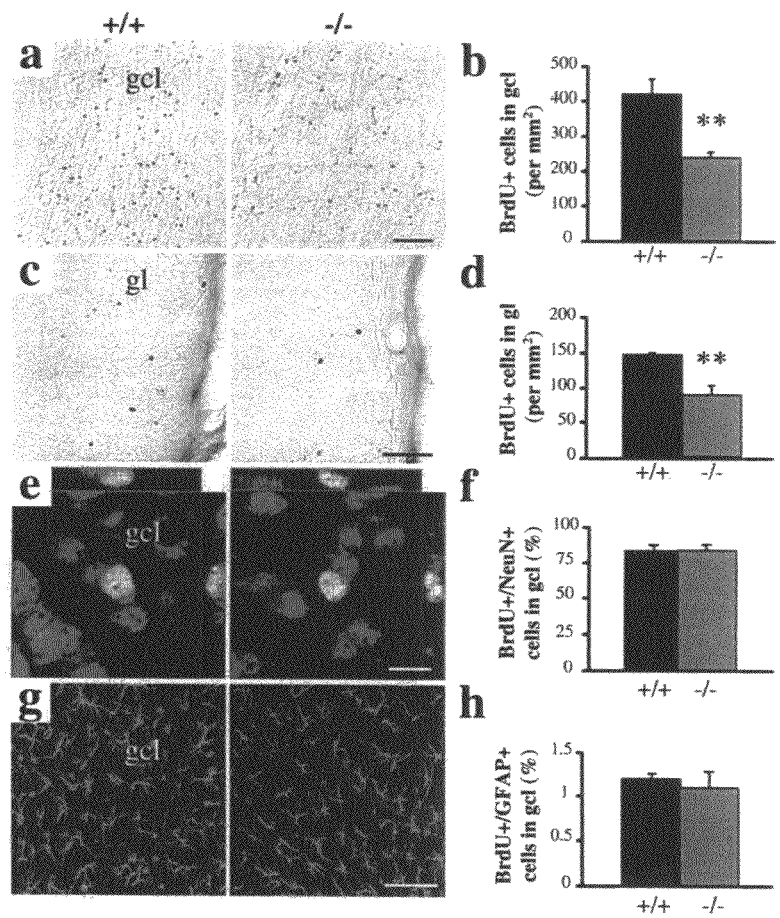
FIG. 4: Reduced density of newborn cells in the OB of TNR-deficient mice, 21 days following BrdU injection. Quantification of BrdU+ nuclei in the GCL (a) and GL (c) of control (left panels) and TNR-deficient (right panels) mice reveals a pronounced reduction in the number of newborn cells in the mutant. Mean densities of newborn granule (b) and periglomerular (d) cells in control (+/+) and TNR-deficient (−/−) mice. **, $P<0.01$. (e) Confocal 3D reconstruction of BrdU+ cells (red) in control (left panel) and TNR-deficient (right panel) mice stained for the neuronal marker NeuN (green). Reconstructed orthogonal projections are presented as viewed in the x-z (top) and y-z (right) planes. (f) Percentage of BrdU+ cells double-labeled with NeuN in control (+/+) and TNR-deficient (−/−) mice. (g) Double immunostaining for BrdU (red) and the astrocytic marker GFAP (green) in the gcl of control (left panel) and TNR-deficient (right panel) mice. (h) Percentage of BrdU+ cells double-labeled with GFAP in control and TNR-deficient mice. In total, 940 (from 3 control animals) and 972 (from 4 TNR-deficient mice) randomly chosen BrdU+ cells were inspected for NeuN immunostaining. Similarly, 836 and 1292 BrdU+ cells were checked for GFAP immunopositivity. GCL, granule cell layer; GL, glomerular layer. Scale bars: a and c, 100 µm; e, 10 µm; g, 50 µm. Values in histograms are means±SEM.

To investigate the potential role of TNR in bulbar neurogenesis, TNR-deficient mice were used. Adult mutant and wild-type mice were given four pulses of BrdU, a marker for DNA synthesis, and brains were processed for BrdU immunohistochemistry 21 days later. Most of the BrdU+ nuclei were found scattered throughout the granule cell layer (FIG. 4a) and, to a lesser extent, in the glomerular layer (FIG. 4c). The mean density of BrdU+ nuclei located in the granule cell layer was significantly lower in mutants than in control mice ($241 \pm 16$ versus $421 \pm 42$ $cells/mm^2$, respectively, n=4 for each genotype, P<0.01; FIG. 4b). A similar effect was also found in the glomerular layer ($90 \pm 12$ versus $148 \pm 2$ $cells/mm^2$, P<0.01; FIG. 4d).

To test whether the 40% reduction seen in TNR-deficient mice was accompanied with alterations in the fate of newborn cells, the proportion of cells double-labeled for BrdU and either the neuronal marker NeuN (FIG. 4e) or the glial marker GFAP (FIG. 4g) was determined. Orthogonal projections through 3D reconstructed BrdU+ cells revealed that, in both genotypes, about 80% of newborn cells were neurons (n=4; FIG. 4f). Similarly, despite the very small number of BrdU+/GFAP+ cells (only approximately 1% of all BrdU+ cells), no difference was seen between genotypes (n=4; FIG. 4h). These results demonstrate that the reduction in the density of BrdU+ cells was similar in the different layers of the mutant OB, but that the fate of newly generated cells remained unchanged.

Example 4

Altered Radial Migration in TNR-Deficient Mice

Figure 5:
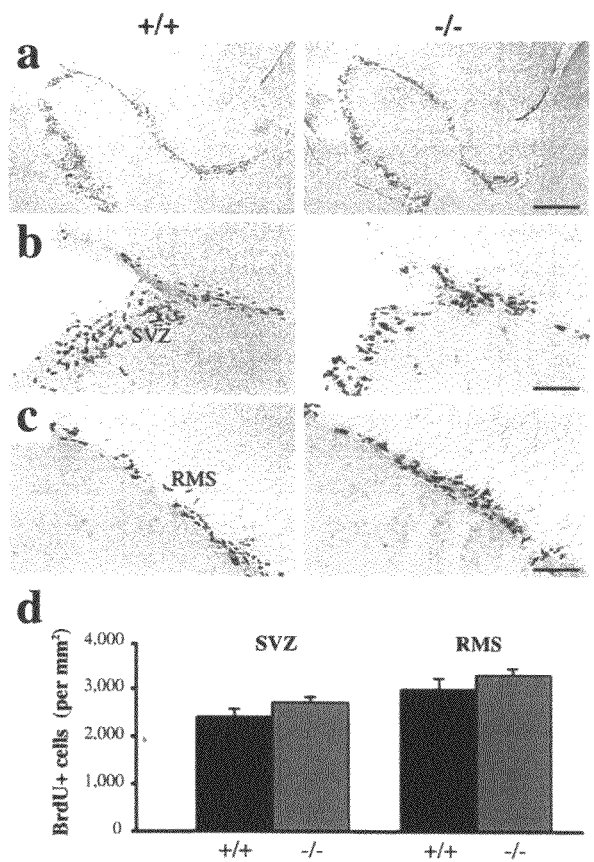
FIG. 5: Normal proliferation in the SVZ and RMS of TNR-deficient mice. (a) BrdU immunostaining in sagittal sections through the forebrain of control (+/+, left panels) and TNR-deficient (−/−, right panels) mice showing the distribution of BrdU+ cells in the SVZ-RMS pathway. High magnification images of the SVZ (b) and RMS (c) indicate similar numbers of mitotically active cells. (d) Quantification of BrdU+ nuclei in the SVZ and the RMS in control (+/+) and TNR-deficient (−/−) mice. Data are presented as means±SEM. Scale bars: a, 500 µm; b and c, 100 µm.

The reduced number of newborn cells in the OB could result from decreased cell proliferation and rate of tangential migration, altered chain organization, distorted radial migration and/or reduced survival of newborn neurons. To assess proliferation, the number of mitotically active cells in the SVZ and the RMS four hours after BrdU injection was quantified. When compared with control animals, the distribution of BrdU+ cells in the SVZ-OB pathway was unchanged in TNR-deficient mice (FIG. 5a). The densities of BrdU+ cells in the SVZ (FIGS. 5b and d) and RMS (FIGS. 5c and d) were undistinguishable between genotypes (2414±156 versus 2721±90 cells/mm$^2$ in the SVZ and 2992±221 versus 3298±138 cells/mm$^2$ in the RMS, for control and mutant mice, respectively; n=3, P>0.05).

Figure 6:
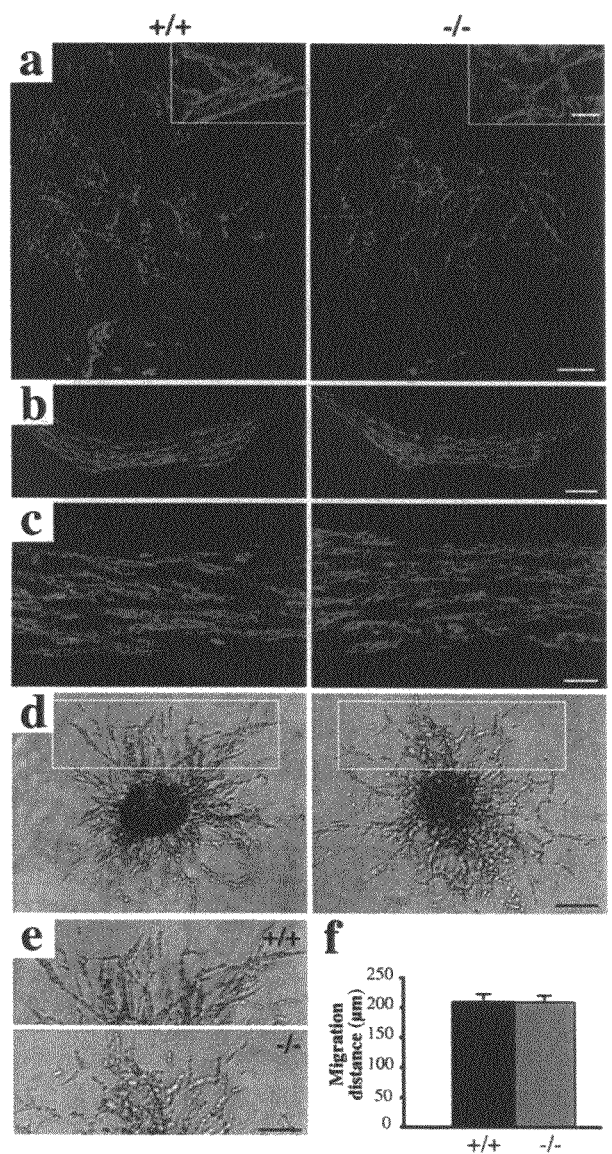
FIG. 6: Normal chain organization and tangential migration of neuroblasts in TNR-deficient mice. (a) Whole-mount immunostaining of PSA-NCAM+ chains in the SVZ of control (+/+, left panels) and TNR-deficient (−/−, right panels) mice. Insets show a high magnification of the PSA-NCAM+ network of chains. PSA-NCAM (green) and BrdU (red) immunostaining in the RMS of control (left panel) and TNR-deficient (right panel) mice at low (b) and high (c) magnifications. (d) Phase-contrast images of SVZ explants of control (left panel) and TNR-deficient (right panel) mice cultured in Matrigel for 20 hours. (e) High magnification images of boxed areas in (d) showing chain organization of neuroblasts migrating out of the SVZ explants. (f) Quantification of migration distance revealed no difference between control (+/+) and TNR-deficient (−/−) explants. Data are presented as means±SEM. Scale bars: a, 100 µm and inset, 40 µm; b and d, 100 µm; c, 30 µm; e, 40 µm.

To assess whether deficiency in TNR affects tangential migration, the cytoarchitecture of the SVZ and RMS was examined. The chains of neuroblasts visualized by PSA-NCAM immunostaining in whole-mount preparations of the SVZ were similar in mutant and control mice (FIG. 6a). At both low and high magnifications, an extensive network of tangential pathways could readily be observed. Most of the chains in this network formed a longitudinal array that was not altered in mutant animals. Similarly, the organization of PSA-NCAM+ chains along the migratory pathway to the OB was the same in both genotypes (FIG. 6b).

To characterize the distribution of newborn cells in these chains, animals received a BrdU injection and were killed two hours later. In both genotypes, double labeling for PSA-NCAM and BrdU revealed the presence of dividing precursors integrated in chains along the entire pathway (FIGS. 6b and c), thus demonstrating that the organization of neuroblast chains is unaffected by the absence of TNR.

SVZ explants were then cultured on Matrigel to assess the rate of neuroblast migration. This technique has previously been adapted for the study tangential cell migration in vitro (Hack et al., 2002; Wichterle, et al., 1997; Chazal et al., 2000). When SVZ explants from P7 control and mutant mice were cultured for 20 hours, an extensive network of chains formed around the explants (FIG. 6d). There was no difference in the general organization of the network of chains (FIGS. 6d and e), and quantification of their length also did not reveal any significant difference (210±12 µm versus 209±11 µm, for control and mutant animals, respectively, 12 explants from four control animals and eight explants from three mutants, P>0.05; FIG. 4f).

Altogether, these results demonstrate that TNR is not involved in proliferation and tangential migration of neuroblasts. This is consistent with our immunohistological observations that TNR is not detectable in the SVZ and RMS. By contrast, high expression of TNR in the adult OB might play a role either in recruiting neuroblasts from the RMS to the OB or in their survival within the OB.

Figure 7:
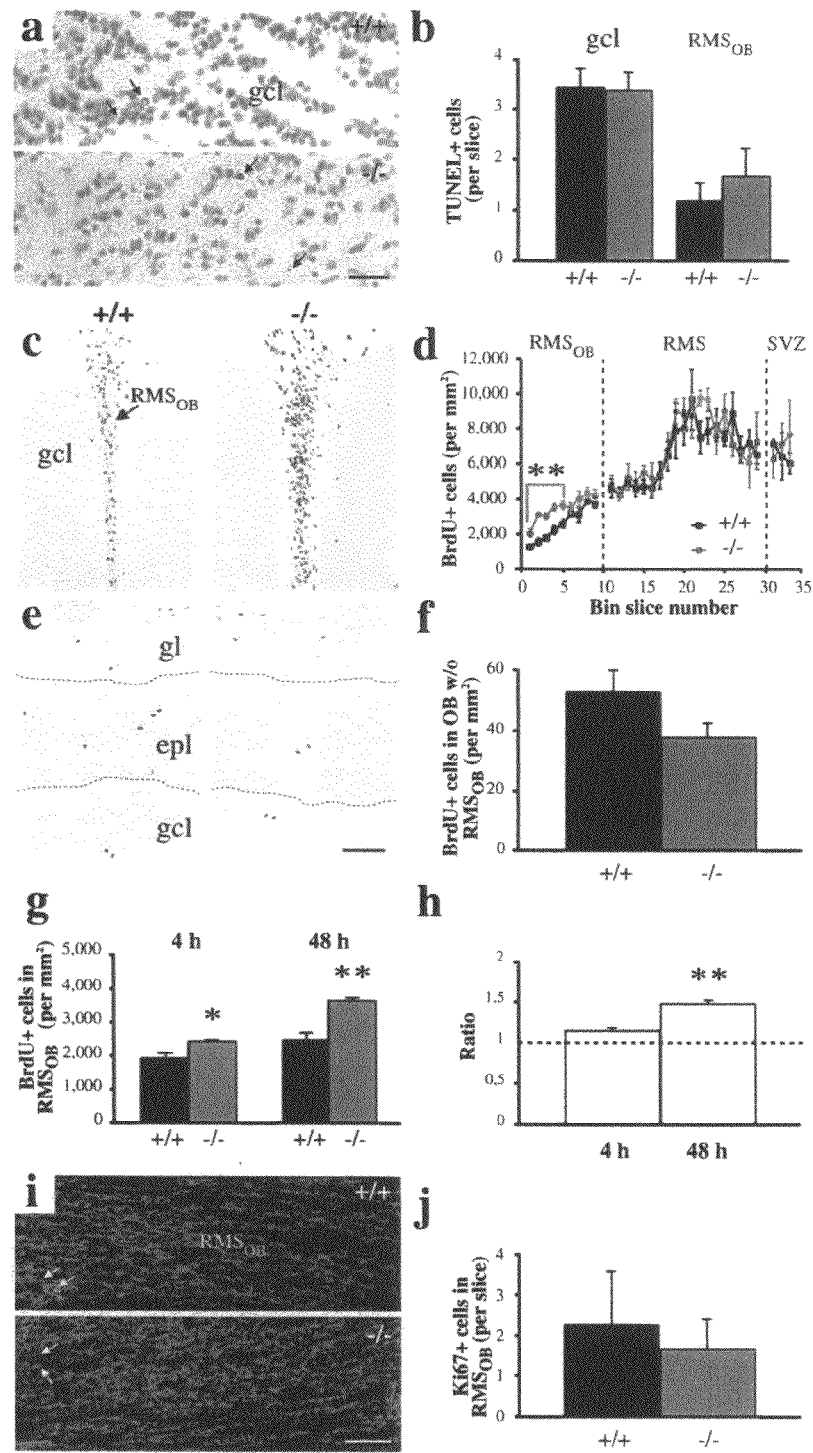
FIG. 7: Abnormal radial migration in the OB of TNR-deficient mice. (a) TUNEL+ nuclei (arrows) in the GCL of control (+/+) and mutant (−/−) mice. (b) Quantification of TUNEL+ nuclei in the GCL and the $RMS_{OB}$ of control and TNR-deficient mice reveals no significant differences in the number of apoptotic cells. (c) BrdU immunostaining in coronal sections of control (left panel) and TNR-deficient (right panel) mice 2 days after BrdU injection. Note the higher density of BrdU+ nuclei in the $RMS_{OB}$ of TNR-deficient mice. (d) Quantification of BrdU+ nuclei in coronal sections from $RMS_{OB}$ to SVZ (120 µm bin size) in control (black squares) and TNR-deficient (grey circles) mice indicates a significant increase in the density of newborn cells exclusively in the $RMS_{OB}$ of TNR-deficient mice. (e) Conversely, a reduced number of newborn cells is seen in the OB of TNR-deficient mice. (f) The total number of BrdU+ nuclei in the OB, excluding the $RMS_{OB}$, is 53±7 versus 38±5 BrdU+ cells/mm$^2$, in control and TNR-deficient mice, respectively. (g) Time-dependent accumulation of neuroblasts in the $RMS_{OB}$ of TNR-deficient as compared to control mice four hours and two days following BrdU injection. (h) Significant increase in the ratio of BrdU+ cells in the $RMS_{OB}$ of TNR-deficient versus control mice measured two days as compared to four hours after BrdU injection. Data are derived by normalizing individual values of TNR-deficient mice to the mean values of controls at each time point. Data are presented as means±SEM. * and ** indicate significant differences of $P<0.05$ and $P<0.01$, respectively. Scale bars: a 50 µm; c and e, 100 µm.

To determine whether granule cells in the OB of mutant mice might be dying at a higher rate than in controls, TUNEL staining was performed to evaluate the level of apoptosis. The number of TUNEL+ cells in both granule cell layer and the RMS$_{OB}$ were quantified (FIGS. 7a and b). Numbers of TUNEL+ cells did not differ between genotypes (3.4±0.4 versus 3.3±0.4 cells/slice in the granule cell layer and 1.2±0.3 versus 1.7±0.5 in the RMS$_{OB}$ of control and mutant mice, respectively; n=3, P>0.05; FIG. 7b). The combined data suggest that the reduced density of BrdU+ cells in the mutant OB results from altered radial migration. If this were the case, the reduced density of newborn cells in the OB should be accompanied by an accumulation of neuroblasts in the RMS$_{OB}$.

Next, an examination was made to determine whether BrdU+ cells would appear "trapped" in the RMS$_{OB}$ of TNR-deficient animals. Animals were killed two days following BrdU injection, and BrdU+ cells were quantified throughout the entire SVZ-OB pathway (FIG. 7d). Newborn cells accumulated exclusively in the RMS$_{OB}$ of mutant mice (FIG. 7c), but not in the RMS or the SVZ (FIG. 7d), confirming that TNR does not affect proliferation and tangential migration. The accumulation of neuroblasts in the RMS$_{OB}$ of TNR-deficient mice was highly significant, when compared to controls (3646±97 and 2470±214 cells/mm$^2$, respectively; n=4; P<0.01; FIGS. 5d and g), and was accompanied by reduced number of BrdU+ cells migrating from the RMS$_{OB}$ to the OB (FIGS. 7e and f). The highest decrease was measured in the external plexiform layer (18±0.8 versus 29.4±4.7 BrdU+ cells/mm$^2$ for mutant and control mice, respectively; P<0.05) and in the glomerular layer (75.1±11.9 versus 104.7±15.3 BrdU+ cells/mm$^2$; P<0.05; FIG. 7e). A lesser, non-significant decrease was found in the granule cell layer (20.1±2.8 versus 24±2 BrdU+ cells/mm$^2$; P>0.05).

To estimate whether excess of BrdU+ cells in the RMS$_{OB}$ of TNR-deficient mice is due to the accumulation of non-migrated cells in that region, the changes in the number of BrdU+ cells in the RMS$_{OB}$ and OB in TNR-deficient mice was compared. TNR-deficient mice had 30.1±7.7 more BrdU+ cells per slice in the RMS$_{OB}$ (105.1±7.7 versus 75±7.1 cells/slice for TNR-deficient and control mice, respectively; P<0.05) and 20.8±9.4 less BrdU+ cells per slice in the OB, including glomerular, external plexiform and granule cells layers, (62.5±4 versus 83.3±9.4 cells/slice for TNR-deficient and control mice, respectively; P<0.05). Interestingly, the total number of BrdU+ cells counted in the OB and RMS$_{OB}$ was not different in TNR-deficient as compared to control animals (167.6±10.5 versus 158.3±15.3 BrdU+ cells per slice for TNR-deficient and control mice, respectively; P>0.05). These results demonstrate that the excess of BrdU+ cells in the RMS$_{OB}$ of TNR-deficient mice is due to the accumulation of non-migrating cells in that region.

Interestingly, in both genotypes, the density of BrdU+ cells in the glomerular layer was quite similar for 2 and 21 days of BrdU post-injection (compare with FIG. 4d). This contrasts sharply with the density of BrdU+ cells counted in the granule cell layer, which increased 20-fold between 2 and 21 days post-injection (compare with FIG. 4b). These results suggest that neuroblasts first migrate predominantly to the glomerular layer before populating the granule cell layer. Thus, this might explain why the density of newborn cells two days after BrdU injection was mainly decreased in the glomerular and external plexiform layers, but only slightly in the granule cell layer of TNR-deficient mice.

Since cell proliferation, tangential migration and cell death were not affected in TNR-deficient mice, the reduced density of newborn neurons in the OB and increased number of neuroblasts in the $RMS_{OB}$ suggest that newborn progenitors are impeded in leaving the $RMS_{OB}$. Thus, the kinetics of accumulation of newborn cells in the $RMS_{OB}$ was tested. When animals were given a pulse of BrdU and sacrificed four hours later, the density of BrdU+ cells in the $RMS_{OB}$ was higher in TNR-deficient mice than in the controls (129.2±11.7 versus 100.7±3 cells/mm²; P<0.05; n=5; FIG. 7g). This increase was even higher two days after BrdU injection (FIG. 7g). Indeed, when the data were expressed as the ratio of mutant to control BrdU+ cell densities in the $RMS_{OB}$, the increase was significantly smaller for the four hour versus two day BrdU post-injection values (respectively, 1.3±0.09 versus 1.5±0.04, P<0.05; FIG. 7h). These results strongly suggest that the absence of TNR leads to an accumulation of newborn cells in the $RMS_{OB}$.

To rule out the possibility that elevated numbers of neuroblasts in the $RMS_{OB}$ of TNR-deficient mice result from increased local proliferation of neuroblast precursors, two sets of experiments were performed. First, by injecting BrdU and sacrificing animals two hours later, dividing progenitors in the SVZ-OB pathway were specifically labeled. The number of BrdU+ cells in the $RMS_{OB}$, stained with PSA-NCAM antibodies, was not different between genotypes (55.0±10.1 versus 49.5±8 cells/mm² for control and TNR-deficient mice, respectively; P>0.05; n=4; see FIG. 11), indicating similar local proliferation rates. In agreement, the number of cells marked by the endogenous cell division marker Ki67 (Tanapat, et al., 1999; Kee et al., 2002) was not different in the $RMS_{OB}$ of control and mutant mice (85.5±50 versus 61.3±28.2 Ki67+ cells/mm²; P>0.05; n=4; see Supplementary FIG. 3b). These results show that absence of TNR reduces the numbers of newborn bulbar neurons due to their accumulation in the $RMS_{OB}$. This highlights the pivotal role for TNR in initiating radial migration.

Example 5

Figure 8:
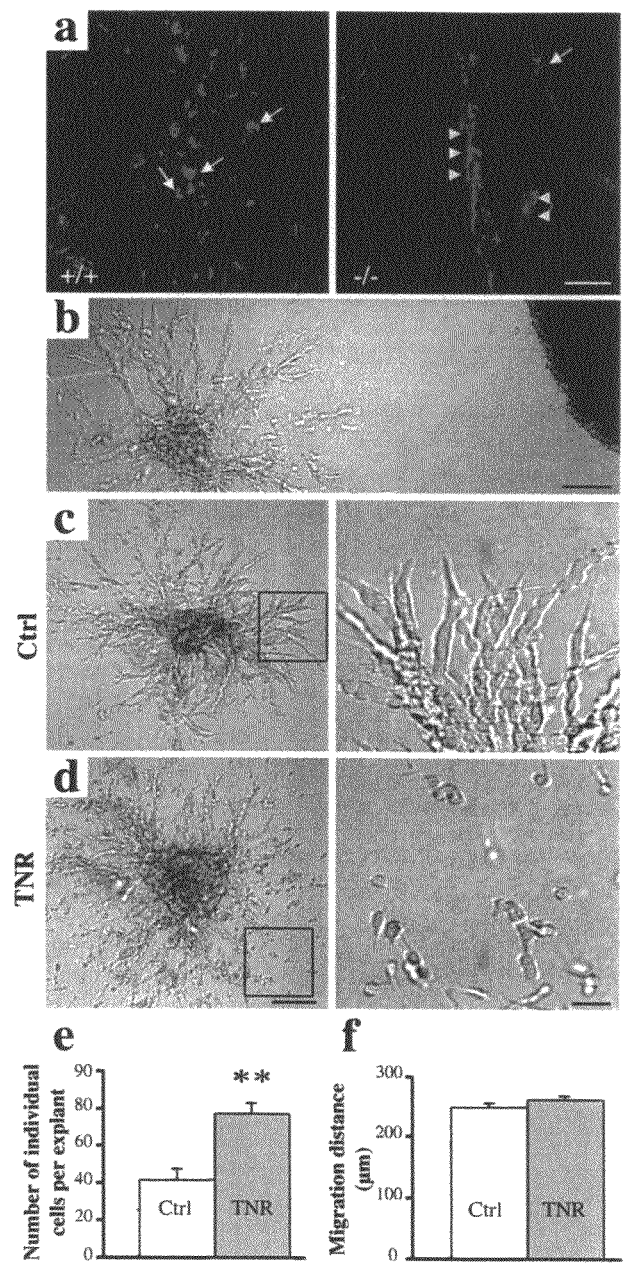
FIG. 8: TNR acts as a detachment signal for tangentially migrating neuroblasts. (a) PSA-NCAM immunostaining in coronal sections of the gcl of control (+/+, left panel) and TNR-deficient (−/−, right panel) mice show that PSA-NCAM+ cells migrate individually (arrows) in control mice, whereas they appear clustered (arrowheads) in TNR-deficient mice. (b) Phase-contrast image showing co-cultures of SVZ explants (left) with an aggregate of BHK cells (right). Examples of SVZ explants co-cultured with BHK cells not secreting (c) and secreting (d) TNR. Right panels are higher magnifications of boxed areas in left panels. Note the increased number of individualized cells in co-cultures of SVZ explants with BHK cells secreting TNR. (e) Significant increase in the number of individualized cells in co-cultures of SVZ explants with BHK cells secreting TNR (41.5±5.8 versus 77±5.9). **, $P<0.001$. (f) Quantification of migration distance of neuroblasts from SVZ explants co-cultured with BHK cells not secreting (Ctrl) or secreting (TNR) TNR. Data are presented as means±SEM. Twenty-one and 27 explants from seven animals were analyzed in cultures without and with TNR, respectively. Scale bars: a and $d_{right}$, 50 µm; b and $d_{left}$, 100 µm.

TNR Promotes Individualization of Neuroblasts and Initiates their Radial Migration Before invading the OB, neuroblasts halt their tangential migration, detach from their migrating chains and leave the $RMS_{OB}$. To examine which of these steps might be regulated by TNR, both in vitro and in vivo approaches were combined. Inspection of PSA-NCAM+ staining at the interface between the $RMS_{OB}$ and granule cell layer showed that most neuroblasts migrate individually in control animals, whereas many clustered in the mutants (FIG. 8a). To assess the role of TNR in stopping tangential migration and detaching neuroblasts from chains, SVZ explants were co-cultured with TNR-expressing or control BHK cells (FIG. 8b-d). When SVZ explants from P7 animals were co-cultured for 20 hours with BHK cells, an extensive network of neuroblasts migrated out of SVZ explants (FIGS. 8c and d). Quantification of the number of individualized neuroblasts per SVZ explant revealed a significantly higher number of such cells in the presence of BHK cells secreting TNR (a 1.9-fold increase, P<0.001; FIG. 8e). Noteworthy is the fact that the migration distance did not differ between control explants (248.5±7.1 µm; 24 explants from eight mice) and those exposed to TNR-secreting cells (260.9±6.5 µm; 29 explants from eight mice) (P=0.2; FIG. 8f). These results indicate that the expression of TNR is instrumental for detaching neuroblasts from chains, but not for halting their tangential migration.

Figure 9:
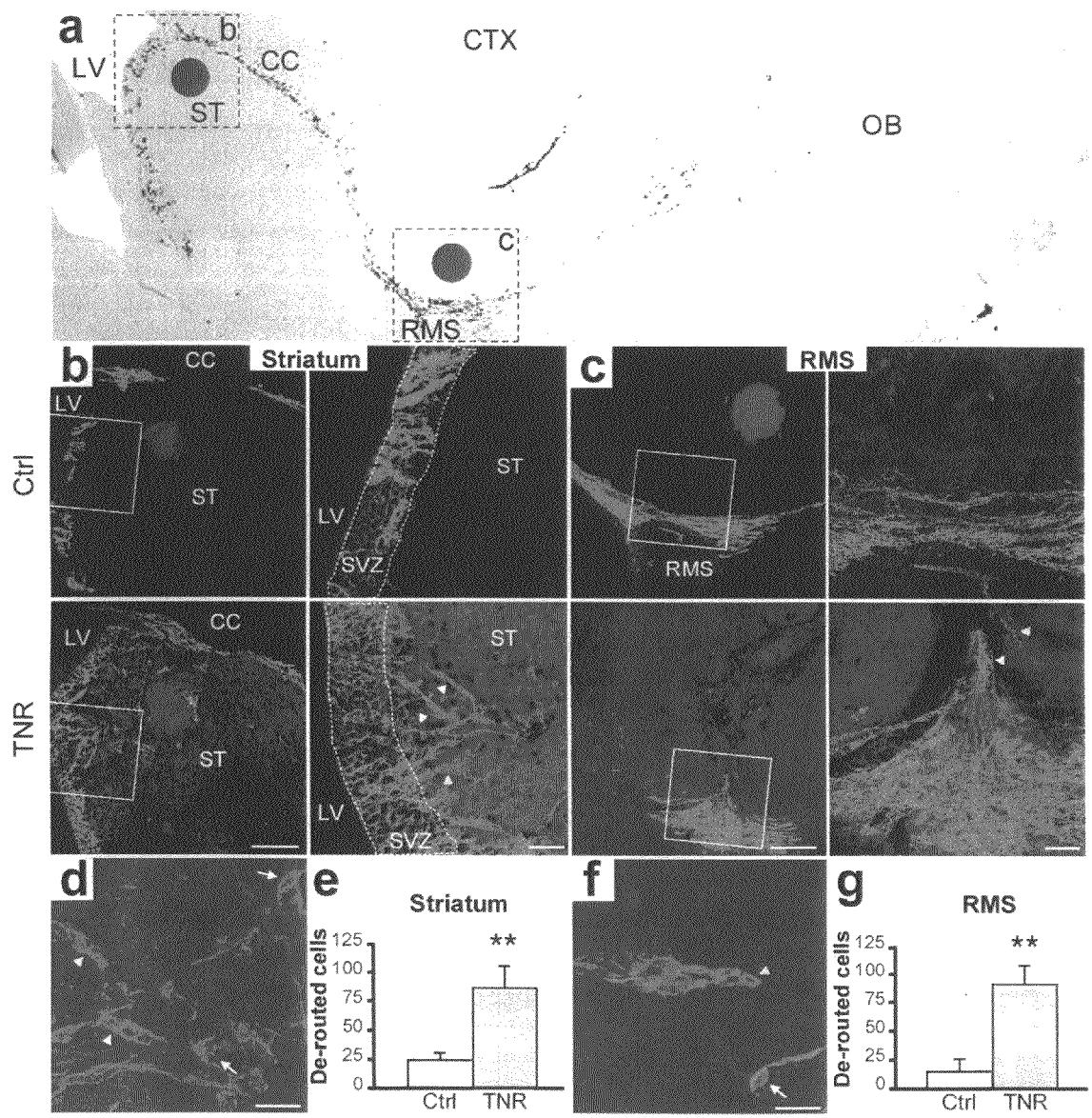
FIG. 9: Ectopic expression of TNR de-routes migrating neuroblasts. (a) BrdU immunostained sagittal section showing the place of BHK cells grafts (red circles). (b) Control (upper panels, Ctrl) or TNR-secreting (lower panels, TNR) BHK cells pre-labeled with PKH26 (red staining) were placed into the striatum neighboring the SVZ. The de-routed neuroblasts were quantified by counting PSA-NCAM+ cells (green staining) in the 400 µm diameter area calculated from the perimeter of the graft. Note the TNR immunopositive areas (blue staining) in animals injected with BHK cells secreting TNR (lower panels). (c) Same as in (b), but control and TNR-transfected BHK cells were grafted into the area just above the horizontal limb of the RMS (hIRMS). Right panels show high magnifications of the boxed areas shown on the left. Arrowheads indicate chains of neuroblasts de-routed from the SVZ (b) or RMS (c). High magnification images of striatum (d) and area just above the hIRMS (f) injected with BHK cells secreting TNR. Arrows and arrowheads indicate, respectively, the individual neuroblasts and chains of progenitor cells de-routed from their normal migratory pathway.

This in vitro assay, however, does not allow one to determine whether TNR also plays a role in the reorientation of tangentially migrating neuroblasts as seen in vivo in the core of the OB. To examine whether TNR is necessary and sufficient to re-route tangentially migrating neuroblasts, TNR was introduced into forebrain regions that are neither populated by progenitor cells nor express TNR (FIG. 9a). TNR-expressing or control BHK cells pre-stained with PKH26 (red labeling in FIGS. 9b and c) were grafted into the striatum (FIG. 9b) or just above the horizontal limb of the RMS (hIRMS) (FIG. 9c). While animals receiving control cells showed unaltered migration (upper panels in FIGS. 9b and c; n=8), all mice grafted with transfected cells (n=7) had neuroblasts (green labeling in FIGS. 9b and c) entering the TNR-containing area (blue staining in lower panels of FIGS. 9b and c). Ectopic expression of TNR yielded a four to six fold increase in the number of neuroblasts migrating out of the SVZ and hIRMS (24.5±6.2 versus 86.7±19.0 and 15.3±10.5 versus 91.9±16.0 for control and TNR-secreting cells injected, respectively, into the striatum and close to the hIRMS; P<0.005; FIGS. 9e and g). Interestingly, while 28.8±5.8% and 35.5±9.3% of neuroblasts that migrated out of SVZ and hIRMS, respectively, were detached from chains (FIGS. 9d and f, arrows), many of the de-routed neuroblasts were still assemble in the chains (FIGS. 9d and f, arrowheads). These results demonstrate that TNR not only promotes detachment of neuroblasts from chains, but also plays an important role in the reorientation of tangentially migrating neuroblasts.

Example 6

Sensory Input Regulates the Level of TNR Expression in the OB

These results revealed that TNR was not only required, but also sufficient to initiate radial migration in the adult forebrain. It was thus decided to investigate whether this important function is regulated in an activity-dependent manner. Since the OB is the first central relay that receives direct inputs from sensory neurons, unilateral odor deprivation was used to test whether expression of TNR is sensitive to the level of sensory activity. Unilateral sensory deprivation resulted in the small, but statistically significant, decrease in TNR mRNA level in the ipsilateral bulb as soon as 1-2 days following nostril occlusion and which reached a maximum at 4-30 days following nostril occlusion (FIGS. 10a and b). Interestingly, the reduction of TNR mRNA level was reversible, since re-opening of the nostril for five days following 20 days of occlusion resulted in the upregulation of TNR mRNA that reached the level of control bulb (FIG. 10b). Concomitantly, the expression level of TNR protein was assessed following 20 days of odor deprivation. It was found that unilateral nostril occlusion also downregulated by 27±6% the protein expression in the GCL (FIGS. 8c and d; n=5). These results indicate that TNR expression is indeed regulated by an activity-dependent mechanism.

To elucidate whether this activity-dependent regulation of TNR expression could have a functional implication in the recruitment of newly generated cells to the OB, the density of BrdU+ cells in the $RMS_{OB}$ of control and occluded bulbs was inspected, two days following BrdU injection. Similar to results obtained from TNR-deficient mice, downregulation of TNR expression by unilateral odor deprivation for 30 days produced an accumulation of neuroblasts in the $RMS_{OB}$ of occluded as compared to the control bulbs (4023.9±209.9 versus 3258.5±228.3 cells/mm² for odor-deprived and control bulbs, respectively; P<0.05; n=5; FIGS. 10e and f). These results suggest that regulation of TNR expression by sensory input plays a key role in the recruitment of newborn neurons to the OB. Importantly, the accumulation of neuroblasts in the $RMS_{OB}$ was less pronounced in the occluded animals as compared to the TNR-deficient mice (123.5±6.4% versus 147.5±4.1%, respectively; P<0.05), showing the correlation between the level of TNR expression in the OB and the degree of neuroblasts accumulation in the $RMS_{OB}$.

REFERENCES

The entire disclosures of each of the following publications are relied upon and incorporated by reference herein:
1. Alvarez-Buylla, A. & Garcia-Verdugo, J. M. Neurogenesis in adult subventricular zone. *J. Neurosci.* 22, 629-634 (2002).
2. Arvidsson, A., Collin, T., Kirik, D., Kokaia, Z. & Lindvall, O. Neuronal replacement from endogenous precursors in the adult brain after stroke. *Nat. Med.* 8, 963-970 (2002).
3. Ausubel et al., (Eds.) In: Current Protocols in Molecular Biology. J. Wiley and Sons, New York, N.Y. (1998).
4. Barany, et al, Intl. J. Peptide Protein Res. 30: 705-739 (1987).
5. Bodasnsky, ed. Peptide Chemistry, A Practical Textbook, Springer-Verlag (1988).
6. Boudreau, N. & Bissell, M. J. Extracellular matrix signaling: integration of form and function in normal and malignant cells. *Curr. Opin. Cell Biol.* 10, 640-646 (1998).
7. Bruckner, G. et al. Postnatal development of perineuronal nets in wild-type mice and in a mutant deficient in tenascin-R. *J. Comp. Neurol.* 428, 616-629 (2000).
8. Brunjes, P. C. Unilateral naris closure and olfactory system development. *Brain Res. Brain Res. Rev.* 19, 146-160 (1994).
9. Carleton, A., Petreanu, L. T., Lansford, R., Alvarez-Buylla, A. & Lledo, P. M. Becoming a new neuron in the adult olfactory bulb. *Nat. Neurosci.* 6, 507-518 (2003).
10. Chazal, G., Durbec, P., Jankovski, A., Rougon, G. & Cremer, H. Consequences of neural cell adhesion molecule deficiency on cell migration in the rostral migratory stream of the mouse. *J. Neurosci.* 20, 1446-1457 (2000).
11. Chen et al., PNAS 91:3054-3057 (1994).
12. Cummings, D. M. & Brunjes, P. C. The effects of variable periods of functional deprivation on olfactory bulb development in rats. *Exp. Neurol.* 148, 360-366 (1997).
13. Cummings, D. M., Henning, H. E. & Brunjes, P. C. Olfactory bulb recovery after early sensory deprivation. *J. Neurosci.* 17, 7433-7440 (1997).
14. Fan, C. M. & Tessier-Lavigne, M. Patterning of mammalian somites by surface ectoderm and notochord: evidence for sclerotome induction by a hedgehog homolog. *Cell* 79, 1175-1186 (1994).
15. Frazier, L. L. & Brunjes, P. C. Unilateral odor deprivation: early postnatal changes in olfactory bulb cell density and number. *J. Comp. Neurol.* 269, 355-370 (1998).
16. Fuss, B., Wintergerst, E. S., Bartsch, U. & Schachner, M. Molecular characterization and in situ mRNA localization of the neural recognition molecule J1-160/180: a modular structure similar to tenascin. *J. Cell Biol.* 120, 1237-1249 (1993).
17. Hack, I., Bancila, M., Loulier, K., Carroll, P. & Cremer, H. Reelin is a detachment signal in tangential chain-migration during postnatal neurogenesis. *Nat. Neurosci.* 5, 939-945 (2002).
18. Henegar, J. R. & Maruniak, J. A. Quantification of the effects of long-term unilateral naris closure on the olfactory bulbs of adult mice. *Brain Res.* 568, 230-234 (1991).
19. Ike et al., Nucl. Acids Res. 11:477 (1983).
20. Itakura et al., Annu Rev Biochem 53:323 (1984a).
21. Itakura et al., Science 198:1056 (1984b).
22. Jones, F. S. & Jones, P. L. The tenascin family of ECM glycoproteins: structure, function, and regulation during embryonic development and tissue remodeling. *Dev. Dyn.* 218, 235-259 (2000).
23. Kaiser, et al, Science 243: 187-198 (1989).
24. Kaufman et al. EMBO J 6: 187-195 (1987).
25. Kee, N., Sivalingam, S., Boonstra, R. & Wojtowicz, J. M. The utility of Ki-67 and BrdU as proliferative markers of adult neurogenesis. *J. Neurosci. Methods* 115, 97-105 (2002).
26. Kennedy, T. E. & Tessier-Lavigne, M. Guidance and induction of branch formation in developing axons by target-derived diffusible factors. *Curr. Opin. Neurobiol.* 5, 83-90 (1995).
27. Kent, Ann. Rev. Biochem. 57:957-989 (1988).
28. Komuro, H. & Rakic, P. Modulation of neuronal migration by NMDA receptors. *Science* 260, 95-97 (1993).
29. Luskin, M. B. Restricted proliferation and migration of postnatally generated neurons derived from the forebrain subventricular zone. *Neuron* 11, 173-189 (1993).
30. Magavi, S. S., Leavitt, B. R. & Macklis, J. D. Induction of neurogenesis in the neocortex of adult mice. *Nature* 405, 951-955 (2000).
31. Meisami, E. Effects of olfactory deprivation on postnatal growth of the rat olfactory bulb utilizing a new method for production of neonatal unilateral anosmia. *Brain Res.* 107, 437-444 (1976).
32. Merrifield, Science 232: 241-247 (1986).
33. Milev, P. et al. High affinity binding and overlapping localization of neurocan and phosphacan/protein-tyrosine phosphatase-zeta/beta with tenascin-R, amphoterin, and the heparin-binding growth-associated molecule. *J. Biol. Chem.* 273, 6998-7005 (1998).
34. Morganti, M. C., Taylor, J., Pesheva, P. & Schachner, M. Oligodendrocyte-derived J1-160/180 extracellular matrix glycoproteins are adhesive or repulsive depending on the partner cell type and time of interaction. *Exp Neurol.* 109, :98-110 (1990).
35. Murase, S. & Horwitz, A. F. Deleted in colorectal carcinoma and differentially expressed integrins mediate the directional migration of neural precursors in the rostral migratory stream. *J. Neurosci.* 22, 3568-3579 (2002).
36. Nakatomi, H. et al. Regeneration of hippocampal pyramidal neurons after ischemic brain injury by recruitment of endogenous neural progenitors. *Cell* 110, 429-441 (2002).
37. Narang, Tetrahedron 39:3 (1983).
38. Nikonenko, A., Schmidt, S., Skibo, G., Bruckner, G. and Schachner, M. Tenascin-R-deficient mice show structural alterations of symmetric perisomatic synapses in the CA1 region of the hippocampus. *J Comp Neurol.* 456, 338-349 (2003).
39. Pesheva, P., Gennarini, G., Goridis, C. & Schachner, M. The F3/11 cell adhesion molecule mediates the repulsion of neurons by the extracellular matrix glycoprotein J1-160/180. *Neuron* 10, 69-82 (1993).
40. Pesheva, P. & Probstmeier, R. The yin and yang of tenascin-R in CNS development and pathology. *Prog. Neurobiol.* 61, 465-493 (2000).
41. Probstmeier, R., Michels, M., Franz, T., Chan, B. M. & Pesheva, P. Tenascin-R interferes with integrin-dependent oligodendrocyte precursor cell adhesion by a ganglioside-mediated signalling mechanism. *Eur. J. Neurosci.* 11, 2474-2488 (1999).
42. Rochefort, C., Gheusi, G., Vincent, J. D. & Lledo, P. M. Enriched odor exposure increases the number of newborn neurons in the adult olfactory bulb and improves odor memory. J. Neurosci. 22, 2679-2689 (2002).

43. Saghatelyan, A. K. et al. Reduced perisomatic inhibition, increased excitatory transmission, and impaired long-term potentiation in mice deficient for the extracellular matrix glycoprotein tenascin-R. *Mol. Cell. Neurosci.* 17, 226-240 (2001).
44. Saghatelyan, A. et al. Recognition molecule associated carbohydrate inhibits postsynaptic GABAb receptors: a mechanism for homeostatic regulation of GABA release in perisomatic synapses. *Mol. Cell. Neurosci.* (in press) (2003).
45. Sambrook, et al., Molecular Cloning: A Laboratory Manual, 2nd ed., (Cold Spring Harbor Laboratory Press; Cold Spring Harbor, N.Y.) (1990).
46. Seed, Nature 329:840 (1987).
47. Srinivasan, J., Schachner, M. & Catterall, W. A. Interaction of voltage-gated sodium channels with the extracellular matrix molecules tenascin-C and tenascin-R. *Proc. Natl. Acad. Sci. USA* 95, 15753-15757 (1998).
48. Svendsen, C. N. & Sofroniew, M. V. Do central nervous system neurons require target-derived neurotrophic support for survival throughout adult life and aging? *Perspect. Dev. Neurobiol.* 3, 133-142 (1996).
49. Tanapat, P., Hastings, N. B., Reeves, A. J. & Gould, E. Estrogen stimulates a transient increase in the number of new neurons in the dentate gyrus of the adult female rat. *J. Neurosci.* 19, 5792-5801 (1999).
50. Thomas, L. B., Gates, M. A. & Steindler, D. A. Young neurons from the adult subependymal zone proliferate and migrate along an astrocyte, extracellular matrix-rich pathway. *Glia* 17, 1-14 (1996).
51. Weber, P. et al. Mice deficient for tenascin-R display alterations of the extracellular matrix and decreased axonal conduction velocities in the CNS. *J. Neurosci.* 19, 4245-4262 (1999).
52. Wichterle, H., Garcia-Verdugo, J. M. & Alvarez-Buylla, A. Direct evidence for homotypic, glia-independent neuronal migration. *Neuron* 18, 779-791 (1997).
53. Xiao, Z. C. et al. Isolation of a tenascin-R binding protein from mouse brain membranes. A phosphacan-related chondroitin sulfate proteoglycan. *J. Biol. Chem.* 272, 32092-32101 (1997).
54. Xiao, Z. C. et al. Defasciculation of neurites is mediated by tenascin-R and its neuronal receptor F3/11. *J. Neurosci. Res.* 52, 390-404 (1998).
55. Xiao, Z. C. et al. Tenascin-R is a functional modulator of sodium channel beta subunits. *J. Bio. Chem.* 274, 26511-26517 (1999).

What is claimed is:

1. A pharmaceutical composition, which comprises
tenascin-R (TNR) in solution in
a pharmaceutically acceptable carrier;
wherein the TNR is in an amount of 0.1 to 1 µg/ml of TNR per ml of solution sufficient to direct migration of neuroblasts within the CNS or within the PNS of a mammal.

2. The pharmaceutical composition of claim 1, wherein the mammal is human.

3. The pharmaceutical composition of claim 1, wherein the mammal is a cow, a horse, a dog, a sheep, a cat, or a mouse.

4. The pharmaceutical composition of claim 1, wherein the composition comprises
tenascin-R (TNR);
at least one compound selected from liposomes, VEGF (vascular endothelial growth factor), interleukins, TNFα (tumor necrosis factor alpha), polyoxyethylene, polyoxyethylene ethers of fatty acids, sorbitan monooleate, sorbitan monolaurate, polyoxyethylene monolaurate, polyoxyethylene sorbitan monolaurate, fusidic acid, EDTA, disodium EDTA, cholic acid, deoxycholic acid, glycocholic acid, glycodeoxycholic acid, taurocholic acid, taurodeoxycholic acid, sodium cholate, sodium glycocholate, glycocholate, sodium deoxycholate, sodium taurocholate, sodium glycodeoxycholate, sodium taurodeoxycholate, chenodeoxycholic acid, urosdeoxycholic acid, saponins, glycyrrhizic acid, ammonium glycyrrhizide, decamethonium, decamethonium bromide, dodecyltrimethylammonium bromide, and dimethyl-β-cyclodextrin, in an amount sufficient to allow the TNR to penetrate into the mammal's brain; and
a pharmaceutically acceptable carrier.

5. The pharmaceutical composition of claim 1, wherein the TNR amino acid sequence has at least 95% identity with SEQ ID NO:2.

6. The pharmaceutical composition of claim 1, wherein the TNR amino acid sequence of SEQ ID NO:2 contains at least one conservative amino acid substitution.

7. The pharmaceutical composition of claim 6, wherein the conservative amino acid substitution is a nonpolar amino acid chosen from alanine, leucine, isoleucine, valine, proline, phenylalanine, tryptophan, and methionine.

8. The pharmaceutical composition of claim 6, wherein the conservative amino acid substitution is a polar neutral amino acid chosen from glycine, serine, threonine, cysteine, tyrosine, asparagine, and glutamine.

9. The pharmaceutical composition of claim 6, wherein the conservative amino acid substitution is a positively charged amino acid chosen from arginine, lysine, and histidine.

10. The pharmaceutical composition of claim 6, wherein the conservative amino acid substitution is a negatively charged amino acid chosen from aspartic acid and glutamic acid.

11. The pharmaceutical composition of claim 1, wherein the TNR is chosen from the 180 kD, 220 kD, 200 kD, 280 kD, and 160 kD forms of TNR.

12. A pharmaceutical composition, wherein the composition comprises
tenascin-R (TNR);
at least one antipyrogenic agent in an amount sufficient to reduce fever in a mammal; and
a pharmaceutically acceptable carrier;
wherein the TNR is in solution in an amount of 0.1 to 1 µg/ml of the TNR per ml of solution sufficient to direct migration of neuroblasts within the CNS or within the PNS of a mammal.

13. The pharmaceutical composition of claim 12, wherein the antipyrogenic agent is selected from cox2 inhibitors, indomethacin, and salicylic acid.

14. The pharmaceutical composition of claim 12, wherein the mammal is human.

15. The pharmaceutical composition of claim 12, wherein the mammal is a cow, a horse, a dog, a sheep, a cat, or a mouse.

16. The pharmaceutical composition of claim 12, wherein the composition comprises
tenascin-R (TNR);
at least one compound selected from liposomes, VEGF (vascular endothelial growth factor), interleukins, TNFα (tumor necrosis factor alpha), polyoxyethylene, polyoxyethylene ethers of fatty acids, sorbitan monooleate, sorbitan monolaurate, polyoxyethylene monolaurate, polyoxyethylene sorbitan monolaurate, fusidic acid, EDTA, disodium EDTA, cholic acid, deoxycholic acid, glycocholic acid, glycodeoxycholic acid, taurocholic acid, taurodeoxycholic acid, sodium cholate, sodium glycocholate, glycocholate, sodium deoxycholate, sodium taurocholate, sodium glycodeoxycholate, sodium taurodeoxycholate, chenodeoxycholic acid, urosdeoxycholic acid, saponins, glycyrrhizic acid, ammonium glycyrrhizide, decamethonium, decamethonium bromide, dodecyltrimethylammonium bromide, and dimethyl-P-cyclodextrin, in an amount sufficient to allow the TNR to penetrate into the mammal's brain.

* * * * *

UNITED STATES PATENT AND TRADEMARK OFFICE
CERTIFICATE OF CORRECTION

PATENT NO.        : 8,481,486 B2
APPLICATION NO.   : 12/232307
DATED             : July 9, 2013
INVENTOR(S)       : Armen Saghatelyan et al.

Page 1 of 1

It is certified that error appears in the above-identified patent and that said Letters Patent is hereby corrected as shown below:

IN THE CLAIMS:

Claim 16, col. 42, line 45,
"dimethyl-P-cyclodextrin" should read --dimethyl-β-cyclodextrin--.

Signed and Sealed this
Twenty-seventh Day of August, 2013

Teresa Stanek Rea
*Acting Director of the United States Patent and Trademark Office*

SEQUENCE LISTING

```
<160> NUMBER OF SEQ ID NOS: 3

<210> SEQ ID NO 1
<211> LENGTH: 4716
<212> TYPE: DNA
<213> ORGANISM: Homo sapiens

<400> SEQUENCE: 1
ccttggtttc cgttgcagat tcccacaact ccatgctgtg tgctgcaggc tggtcctgaa      60
cccagatctc tggctgagag gatggggggca gatggggaaa cagtggttct gaagaacatg     120
ctcattggcg tcaacctgat ccttctgggc tccatgatca agccttcaga gtgtcagctg     180
gaggtcacca cagaaagggt ccagagacag tcagtggagg aggagggagg cattgccaac     240
tacaacacgt ccagcaaaga gcagcctgtg gtcttcaacc acgtgtacaa cattaacgtg     300
cccttggaca acctctgctc ctcagggcta gaggcctctg ctgagcagga ggtgagtgca     360
gaagacgaga ctctggcaga gtacatgggc cagacctcag accacgagag ccaggtcacc     420
tttacacaca ggatcaactt ccccaaaaag gcctgtccat gtgccagttc agcccaggtg     480
ctgcaggagc tgctgagccg gatcgagatg ctggagaggg aggtgtcggt gctgcgagac     540
cagtgcaacg ccaactgctg ccaagaaagt gctgccacag acaactggac ctatatccct     600
cactgcagtg gccacggcaa ctttagcttt gagtcctgtg gctgcatctg caacgaaggc     660
tggtttggca agaattgctc ggagcccttac tgcccgctgg gttgctccag ccgggggggtg     720 tgtgtggatg gccagtgcat ctgtgacagc gaatacagcg gggatgactg ttccgaactc     780
cggtgcccaa cagactgcag ctcccggggg ctctgcgtgg acgggggagtg tgtctgtgaa     840 gagccctaca ctggcgagga ctgcagggaa ctgaggtgcc ctgggggactg ttcggggaag     900 gggagatgtg ccaacggtac ctgtttatgc gaggagggct acgttggtga ggactgcggc     960
cagcggcagt gtctgaatgc ctgcagtggg cgaggacaat gtgaggaggg gctctgcgtc    1020
tgtgaagagg gctaccaggg ccctgactgc tcagcagttg cccctccaga ggacttgcga    1080
```

```
gtggctggta tcagcgacag gtccattgag ctggaatggg acgggccgat ggcagtgacg      1140
gaatatgtga tctcttacca gccgacggcc ctgggggggcc tccagctcca gcagcgggtg     1200
cctggagatt ggagtggtgt caccatcacg gagctggagc caggtctcac ctacaacatc     1260
agcgtctacg ctgtcattag caacatcctc agccttccca tcactgccaa ggtggccacc     1320
catctctcca ctcctcaagg gctacaattt aagacgatca cagagaccac cgtggaggtg     1380
cagtgggagc ccttctcatt ttccttcgat gggtgggaaa tcagcttcat tccaaagaac     1440
aatgaagggg gagtgattgc tcaggtcccc agcgatgtta cgtcctttaa ccagacagga     1500
ctaaagcctg gggaggaata cattgtcaat gtggtggctc tgaaagaaca ggcccgcagc     1560
ccccctacct cggccagcgt ctccacagtc attgacggcc ccacgcagat cctggttcgc     1620
gatgtctcgg acaccgtggc ttttgtggag tggattcccc ctcgagccaa agtcgatttc     1680
attcttttga atatggcct ggtgggcggg aaggtggga ggaccacctt ccggctgcag       1740
cctcccctga gccaatactc agtgcaggcc ctgcggcctg gctcccgata cgaggtgtca     1800
gtcagtgccg tccgagggac caacgagagc gattctgcca ccactcagtt cacaacagag     1860
atcgatgccc ccaagaactt gcgagttggt tctcgcacag caaccagcct tgacctcgag     1920
tgggataaca gtgaagccga agttcaggag tacaaggttg tgtacagcac cctggcgggt     1980
gagcaatatc atgaggtact ggtccccagg ggcattggtc aaccaccag ggccaccctg      2040 acagatctgg tacctggcac tgagtatgga gttggaatat ctgccgtcat gaactcacag     2100
caaagcgtgc cagccaccat gaatgccagg actgaacttg acagtccccg agacctcatg     2160
gtgacagcct cctcggagac ctccatctcc ctcatctgga ccaaggccag tggccccatt     2220
gaccactacc gaattacctt taccccatcc tctgggattg cctcagaagt caccgtaccc     2280
aaggacagga cctcatacac actaacagat ctagagcctg gggcagagta catcatttcc     2340
gtcactgctg agaggggtcg gcagcagagc ttggagtcca ctgtggatgc tttcacaggc     2400
ttccgtccca tctctcatct gcacttttct catgtgacct cctccagtgt gaacatcact     2460
tggagtgatc catctccccc agcagacaga ctcattctta actacagccc cagggatgag     2520
gaggaagaga tgatggaggt ctccctggat gccaccaaga gcatgctgt cctgatgggc      2580 ctgcaaccag ccacagagta tattgtgaac cttgtggctg tccatggcac agtgacctct     2640
gagcccattg tgggctccat caccacagga attgatcccc caaaagacat cacaattagc     2700
aatgtgacca aggactcagt gatggtctcc tggagccctc tgttgcatc tttcgattac     2760 taccgagtat catatcgacc cacccaagtg ggacgactag acagctcagt ggtgcccaac     2820
actgtgacag aattcaccat caccagactg aacccagcta ccgaatacga aatcagcctc     2880
aacagcgtgc ggggcaggga ggaaagcgag cgcatctgta ctcttgtgca cacagccatg     2940
gacaaccctg tggatctgat tgctaccaat atcactccaa cagaagccct gctgcagtgg     3000
aaggcaccag tgggtgaggt ggagaactac gtcattgttc ttacacactt tgcagtcgct     3060
ggagagacca tccttgttga cggagtcagt gaggaatttc ggcttgttga cctgcttcct     3120
agcacccact atactgccac catgtatgcc accaatggac ctctcaccag tggcaccatc     3180
agcaccaact tttctactct cctggaccct ccggcaaacc tgacagccag tgaagtcacc     3240
agacaaagtg ccctgatctc ctggcagcct cccagggcag agattgaaaa ttatgtcttg     3300
acctacaaat ccaccgacgg aagccgcaag gagctgattg tggatgcaga agacacctgg     3360
attgactggg agggcctgtt ggagaacaca gactacacgg tgctcctgca ggcagcacag     3420
gacaccacgt ggagcagcat cacctccacc gctttcacca caggaggccg ggtgttccct     3480
```

```
catccccaag actgtgccca gcatttgatg aatggagaca ctttgagtgg ggtttacccc    3540
atcttcctca atggggagct gagccagaaa ttacaagtgt actgtgatat gaccaccgac    3600
gggggcggct ggattgtatt ccagaggcgg cagaatggcc aaactgattt tttccggaaa    3660
tgggctgatt accgtgttgg cttcgggaac gtggaggatg agttctggct ggggctggac    3720
aatatacaca ggatcacatc ccagggccgc tatgagctgc gcgtggacat gcgggatggc    3780
caggaggccg ccttcgcctc ctacgacagg ttctctgtcg aggacagcag aaacctgtac    3840
aaactccgca taggaagcta acggcact gcggggact ccctcagcta tcatcaagga    3900 cgcccttttct ccacagagga tagagacaat gatgttgcag tgactaactg tgccatgtcg    3960
tacaagggag catggtggta taagaactgc caccggacca acctcaatgg gaagtacggg    4020
gagtccaggc acagtcaggg catcaactgg taccattgga aaggccatga gttctccatc    4080 cccttttgtgg aaatgaagat gcgcccctac aaccaccgtc tcatggcagg agaaaacgg    4140 cagtccttac agttctgagc agtgggcggc tgcaagccaa ccaatatttt ctgtcatttg    4200
tttgtatttt ataatatgaa acaagggggg agggtaatag caatgtgttt tgcaacatat    4260
taagagtatg tgaaggaagc agggatgtcg caggaatccg ctggctaaca tctgctcttg    4320
gtttctgctg ccctggagcc tgaccctcag tctccattct ccctcctacc caggcctcct    4380
caaccttcac ctccttccc accaaggagg agaagtagga agttttctta aagggccaat    4440
tcaaagccaa gtcgtggggt gcagattgtt atggtgacag gcacacacat ttttctaccc    4500
ttcttctgag atgtcctctg ccttccaggt atttgtgatt ttgtcacagc ctgacatggc    4560
caggttctca cactggccca gagaaaagag cctcagcaag agagttttgc caacaattcc    4620
ccttaaaagg aaacagatca actacaccgc atcccaacaa cccaggttct tttccttcct    4680
tccttccttc ctcccttcct tctttcctgc cttccc                              4716
```

<210> SEQ ID NO 2
<211> LENGTH: 1358
<212> TYPE: PRT
<213> ORGANISM: Homo sapiens

<400> SEQUENCE: 2

```
Met Gly Ala Asp Gly Glu Thr Val Val Leu Lys Asn Met Leu Ile Gly
  1               5                  10                  15

Val Asn Leu Ile Leu Leu Gly Ser Met Ile Lys Pro Ser Glu Cys Gln
                 20                  25                  30

Leu Glu Val Thr Thr Glu Arg Val Gln Arg Gln Ser Val Glu Glu Glu
             35                  40                  45

Gly Gly Ile Ala Asn Tyr Asn Thr Ser Ser Lys Glu Gln Pro Val Val
         50                  55                  60

Phe Asn His Val Tyr Asn Ile Asn Val Pro Leu Asp Asn Leu Cys Ser
 65                  70                  75                  80

Ser Gly Leu Glu Ala Ser Ala Glu Gln Glu Val Ser Ala Glu Asp Glu
                 85                  90                  95

Thr Leu Ala Glu Tyr Met Gly Gln Thr Ser Asp His Glu Ser Gln Val
            100                 105                 110

Thr Phe Thr His Arg Ile Asn Phe Pro Lys Lys Ala Cys Pro Cys Ala
        115                 120                 125

Ser Ser Ala Gln Val Leu Gln Glu Leu Leu Ser Arg Ile Glu Met Leu
    130                 135                 140

Glu Arg Glu Val Ser Val Leu Arg Asp Gln Cys Asn Ala Asn Cys Cys
145                 150                 155                 160
```

-continued

```
Gln Glu Ser Ala Ala Thr Gly Gln Leu Asp Tyr Ile Pro His Cys Ser
                165                 170                 175
Gly His Gly Asn Phe Ser Phe Glu Ser Cys Gly Cys Ile Cys Asn Glu
            180                 185                 190
Gly Trp Phe Gly Lys Asn Cys Ser Glu Pro Tyr Cys Pro Leu Gly Cys
        195                 200                 205
Ser Ser Arg Gly Val Cys Val Asp Gly Gln Cys Ile Cys Asp Ser Glu
    210                 215                 220
Tyr Ser Gly Asp Asp Cys Ser Glu Leu Arg Cys Pro Thr Asp Cys Ser
225                 230                 235                 240
Ser Arg Gly Leu Cys Val Asp Gly Glu Cys Val Cys Glu Glu Pro Tyr
                245                 250                 255
Thr Gly Glu Asp Cys Arg Glu Leu Arg Cys Pro Gly Asp Cys Ser Gly
            260                 265                 270
Lys Gly Arg Cys Ala Asn Gly Thr Cys Leu Cys Glu Glu Gly Tyr Val
        275                 280                 285
Gly Glu Asp Cys Gly Gln Arg Gln Cys Leu Asn Ala Cys Ser Gly Arg
    290                 295                 300
Gly Gln Cys Glu Glu Gly Leu Cys Val Cys Glu Glu Gly Tyr Gln Gly
305                 310                 315                 320
Pro Asp Cys Ser Ala Val Ala Pro Pro Glu Asp Leu Arg Val Ala Gly
                325                 330                 335
Ile Ser Asp Arg Ser Ile Glu Leu Glu Trp Asp Gly Pro Met Ala Val
            340                 345                 350
Thr Glu Tyr Val Ile Ser Tyr Gln Pro Thr Ala Leu Gly Gly Leu Gln
        355                 360                 365
Leu Gln Gln Arg Val Pro Gly Asp Trp Ser Gly Val Thr Ile Thr Glu
    370                 375                 380
Leu Glu Pro Gly Leu Thr Tyr Asn Ile Ser Val Tyr Ala Val Ile Ser
385                 390                 395                 400
Asn Ile Leu Ser Leu Pro Ile Thr Ala Lys Val Ala Thr His Leu Ser
                405                 410                 415
Thr Pro Gln Gly Leu Gln Phe Lys Thr Ile Thr Glu Thr Thr Val Glu
            420                 425                 430
Val Gln Trp Glu Pro Phe Ser Phe Ser Phe Asp Gly Trp Glu Ile Ser
        435                 440                 445
Phe Ile Pro Lys Asn Asn Glu Gly Gly Val Ile Ala Gln Val Pro Ser
    450                 455                 460
Asp Val Thr Ser Phe Asn Gln Thr Gly Leu Lys Pro Gly Glu Glu Tyr
465                 470                 475                 480
Ile Val Asn Val Val Ala Leu Lys Glu Gln Ala Arg Ser Pro Pro Thr
                485                 490                 495
Ser Ala Ser Val Ser Thr Val Ile Asp Gly Pro Thr Gln Ile Leu Val
            500                 505                 510
Arg Asp Val Ser Asp Thr Val Ala Phe Val Glu Trp Ile Pro Pro Arg
        515                 520                 525
Ala Lys Val Asp Phe Ile Leu Leu Lys Tyr Gly Leu Val Gly Gly Glu
    530                 535                 540
Gly Gly Arg Thr Thr Phe Arg Leu Gln Pro Pro Leu Ser Gln Tyr Ser
545                 550                 555                 560
Val Gln Ala Leu Arg Pro Gly Ser Arg Tyr Glu Val Ser Val Ser Ala
                565                 570                 575
Val Arg Gly Thr Asn Glu Ser Asp Ser Ala Thr Thr Gln Phe Thr Thr
            580                 585                 590
```

```
Glu Ile Asp Ala Pro Lys Asn Leu Arg Val Gly Ser Arg Thr Ala Thr
        595                 600                 605
Ser Leu Asp Leu Glu Trp Asp Asn Ser Glu Ala Glu Val Gln Glu Tyr
        610                 615                 620
Lys Val Val Tyr Ser Thr Leu Ala Gly Glu Gln Tyr His Glu Val Leu
625                 630                 635                 640
Val Pro Arg Gly Ile Gly Pro Thr Thr Arg Ala Thr Leu Thr Asp Leu
                    645                 650                 655
Val Pro Gly Thr Glu Tyr Gly Val Gly Ile Ser Ala Val Met Asn Ser
                660                 665                 670
Gln Gln Ser Val Pro Ala Thr Met Asn Ala Arg Thr Glu Leu Asp Ser
            675                 680                 685
Pro Arg Asp Leu Met Val Thr Ala Ser Ser Glu Thr Ser Ile Ser Leu
        690                 695                 700
Ile Trp Thr Lys Ala Ser Gly Pro Ile Asp His Tyr Arg Ile Thr Phe
705                 710                 715                 720
Thr Pro Ser Ser Gly Ile Ala Ser Glu Val Thr Val Pro Lys Asp Arg
                    725                 730                 735
Thr Ser Tyr Thr Leu Thr Asp Leu Glu Pro Gly Ala Glu Tyr Ile Ile
                740                 745                 750
Ser Val Thr Ala Glu Arg Gly Arg Gln Gln Ser Leu Glu Ser Thr Val
            755                 760                 765
Asp Ala Phe Thr Gly Phe Arg Pro Ile Ser His Leu His Phe Ser His
        770                 775                 780
Val Thr Ser Ser Ser Val Asn Ile Thr Trp Ser Asp Pro Ser Pro Pro
785                 790                 795                 800
Ala Asp Arg Leu Ile Leu Asn Tyr Ser Pro Arg Asp Glu Glu Glu Glu
                    805                 810                 815
Met Met Glu Val Ser Leu Asp Ala Thr Lys Arg His Ala Val Leu Met
                820                 825                 830
Gly Leu Gln Pro Ala Thr Glu Tyr Ile Val Asn Leu Val Ala Val His
            835                 840                 845
Gly Thr Val Thr Ser Glu Pro Ile Val Gly Ser Ile Thr Thr Gly Ile
        850                 855                 860
Asp Pro Pro Lys Asp Ile Thr Ile Ser Asn Val Thr Lys Asp Ser Val
865                 870                 875                 880
Met Val Ser Trp Ser Pro Pro Val Ala Ser Phe Asp Tyr Tyr Arg Val
                    885                 890                 895
Ser Tyr Arg Pro Thr Gln Val Gly Arg Leu Asp Ser Ser Val Val Pro
                900                 905                 910
Asn Thr Val Thr Glu Phe Thr Ile Thr Arg Leu Asn Pro Ala Thr Glu
            915                 920                 925
Tyr Glu Ile Ser Leu Asn Ser Val Arg Gly Arg Glu Glu Ser Glu Arg
        930                 935                 940
Ile Cys Thr Leu Val His Thr Ala Met Asp Asn Pro Val Asp Leu Ile
945                 950                 955                 960
Ala Thr Asn Ile Thr Pro Thr Glu Ala Leu Leu Gln Trp Lys Ala Pro
                    965                 970                 975
Val Gly Glu Val Glu Asn Tyr Val Ile Val Leu Thr His Phe Ala Val
                980                 985                 990
Ala Gly Glu Thr Ile Leu Val Asp Gly Val Ser Glu Glu Phe Arg Leu
            995                 1000                1005
Val Asp Leu Leu Pro Ser Thr His Tyr Thr Ala Thr Met Tyr Ala Thr
```

```
                    1010            1015            1020

Asn Gly Pro Leu Thr Ser Gly Thr Ile Ser Thr Asn Phe Ser Thr Leu
1025            1030            1035            1040

Leu Asp Pro Pro Ala Asn Leu Thr Ala Ser Glu Val Thr Arg Gln Ser
            1045            1050            1055

Ala Leu Ile Ser Trp Gln Pro Pro Arg Ala Glu Ile Glu Asn Tyr Val
        1060            1065            1070

Leu Thr Tyr Lys Ser Thr Asp Gly Ser Arg Lys Glu Leu Ile Val Asp
    1075            1080            1085

Ala Glu Asp Thr Trp Ile Arg Leu Glu Gly Leu Leu Glu Asn Thr Asp
    1090            1095            1100

Tyr Thr Val Leu Leu Gln Ala Ala Gln Asp Thr Thr Trp Ser Ser Ile
1105            1110            1115            1120

Thr Ser Thr Ala Phe Thr Thr Gly Gly Arg Val Phe Pro His Pro Gln
            1125            1130            1135

Asp Cys Ala Gln His Leu Met Asn Gly Asp Thr Leu Ser Gly Val Tyr
        1140            1145            1150

Pro Ile Phe Leu Asn Gly Glu Leu Ser Gln Lys Leu Gln Val Tyr Cys
    1155            1160            1165

Asp Met Thr Thr Asp Gly Gly Gly Trp Ile Val Phe Gln Arg Arg Gln
    1170            1175            1180

Asn Gly Gln Thr Asp Phe Phe Arg Lys Trp Ala Asp Tyr Arg Val Gly
1185            1190            1195            1200

Phe Gly Asn Val Glu Asp Glu Phe Trp Leu Gly Leu Asp Asn Ile His
            1205            1210            1215

Arg Ile Thr Ser Gln Gly Arg Tyr Glu Leu Arg Val Asp Met Arg Asp
        1220            1225            1230

Gly Gln Glu Ala Ala Phe Ala Ser Tyr Asp Arg Phe Ser Val Glu Asp
    1235            1240            1245

Ser Arg Asn Leu Tyr Lys Leu Arg Ile Gly Ser Tyr Asn Gly Thr Ala
    1250            1255            1260

Gly Asp Ser Leu Ser Tyr His Gln Gly Arg Pro Phe Ser Thr Glu Asp
1265            1270            1275            1280

Arg Asp Asn Asp Val Ala Val Thr Asn Cys Ala Met Ser Tyr Lys Gly
            1285            1290            1295

Ala Trp Trp Tyr Lys Asn Cys His Arg Thr Asn Leu Asn Gly Lys Tyr
        1300            1305            1310

Gly Glu Ser Arg His Ser Gln Gly Ile Asn Trp Tyr His Trp Lys Gly
    1315            1320            1325

His Glu Phe Ser Ile Pro Phe Val Glu Met Lys Met Arg Pro Tyr Asn
    1330            1335            1340

His Arg Leu Met Ala Gly Arg Lys Arg Gln Ser Leu Gln Phe
1345            1350            1355

<210> SEQ ID NO 3
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
aagcccctcc ttcctcctcc acagtttgtc tctgagccct ttctg            45
```